US011185321B2

United States Patent
Oba et al.

(10) Patent No.: US 11,185,321 B2
(45) Date of Patent: Nov. 30, 2021

(54) SUTURE CLIP DEPLOYMENT DEVICES

(71) Applicant: Edwards Lifesciences Corporation, Irvine, CA (US)

(72) Inventors: Travis Zenyo Oba, Yorba Linda, CA (US); Michael C. Murad, Corona, CA (US); Manouchehr A. Miraki, Laguna Hills, CA (US); Anthony P. Carcia, Portland, OR (US); Fabian Daniel Schroeder, San Diego, CA (US); Raffaele Mazzei, Carlsbad, CA (US); Tyler Douglas Smith, Corvallis, OR (US)

(73) Assignee: Edwards Lifesciences Corporation, Irvine, CA (US)

( * ) Notice: Subject to any disclaimer, the term of this patent is extended or adjusted under 35 U.S.C. 154(b) by 360 days.

(21) Appl. No.: 16/436,829

(22) Filed: Jun. 10, 2019

(65) Prior Publication Data

US 2019/0290261 A1  Sep. 26, 2019

Related U.S. Application Data

(60) Division of application No. 15/385,203, filed on Dec. 20, 2016, now Pat. No. 10,314,573, which is a
(Continued)

(51) Int. Cl.
*A61B 17/04* (2006.01)
*A61B 90/30* (2016.01)
(Continued)

(52) U.S. Cl.
CPC ...... *A61B 17/0487* (2013.01); *A61B 17/0467* (2013.01); *A61B 17/0469* (2013.01);
(Continued)

(58) Field of Classification Search
CPC .. A61B 2017/0488; A61B 2017/00867; A61B 2017/00783; A61B 2017/00561;
(Continued)

(56) References Cited

U.S. PATENT DOCUMENTS 2,264,679 A   12/1941  Ravel
2,516,710 A   7/1950   Mascolo
(Continued)

FOREIGN PATENT DOCUMENTS

CA  2141911  4/2002
CA  2141913  4/2002
(Continued)

OTHER PUBLICATIONS

European Search Report issued for Application No. 12858766.4, dated Sep. 16, 2015.
(Continued)

*Primary Examiner* — Jocelin C Tanner
(74) *Attorney, Agent, or Firm* — Klarquist Sparkman, LLP

(57) ABSTRACT

Suture clip deployment devices for applying suture clips to sutures are described. Some embodiments can include a generally tubular main body and a vacuum port located at the distal end, a hollow inner body longitudinally slidable within the main body and extending from the main body at its distal end, and a suture recess located in the generally tubular main body. At least one suture clip configured to frictionally fit on an outer surface of the inner body is deployed during use. Clip deployment can occur after a vacuum source is applied to the device so as to draw the suture into the device. The suture lines can be retrieved through the suture recess, and the device can be actuated so as to deliver the suture clip off the delivery device and onto the suture, locking the suture in place.

10 Claims, 31 Drawing Sheets

Related U.S. Application Data continuation of application No. 14/658,575, filed on Mar. 16, 2015, now Pat. No. 9,549,730, which is a continuation of application No. 13/715,640, filed on Dec. 14, 2012, now Pat. No. 9,017,347.

(60) Provisional application No. 61/579,497, filed on Dec. 22, 2011.

(51) Int. Cl.
*A61B 1/04* (2006.01)
*A61B 17/00* (2006.01)

(52) U.S. Cl.
CPC ............ *A61B 17/0482* (2013.01); *A61B 1/04* (2013.01); *A61B 90/30* (2016.02); *A61B 2017/00526* (2013.01); *A61B 2017/00561* (2013.01); *A61B 2017/00783* (2013.01); *A61B 2017/00867* (2013.01); *A61B 2017/0488* (2013.01)

(58) Field of Classification Search
CPC .......... A61B 2017/00526; A61B 90/30; A61B 17/0487; A61B 17/0482; A61B 17/0469; A61B 17/0467; A61B 1/04
See application file for complete search history.

(56) References Cited

U.S. PATENT DOCUMENTS

| | | |
|---|---|---|
| 2,715,486 A | 8/1955 | Marcoff-Moghadam et al. |
| 2,890,519 A | 6/1959 | Storz, Jr. |
| 3,143,742 A | 8/1964 | Cromie |
| 3,249,104 A | 5/1966 | Hohnstein |
| 3,274,658 A | 9/1966 | Pile |
| 3,452,742 A | 7/1969 | Muller |
| 3,506,012 A | 4/1970 | Brown |
| 3,509,882 A | 5/1970 | Blake |
| 3,541,591 A | 11/1970 | Hoegerman |
| 3,547,103 A | 12/1970 | Cook |
| 3,570,497 A | 3/1971 | Lemole |
| 3,608,095 A | 9/1971 | Barry |
| 3,638,654 A | 2/1972 | Akuba |
| RE27,391 E | 6/1972 | Merser |
| 3,753,438 A | 8/1973 | Wood et al. |
| 3,859,668 A | 1/1975 | Anderson |
| 3,875,648 A | 4/1975 | Bone |
| 3,898,999 A | 8/1975 | Haller |
| 3,910,281 A | 10/1975 | Kletschka et al. |
| 3,954,109 A | 5/1976 | Patel |
| 3,958,576 A | 5/1976 | Komiya |
| 3,976,079 A | 8/1976 | Samuels et al. |
| 3,988,810 A | 11/1976 | Emery |
| 3,996,623 A | 12/1976 | Kaster |
| 4,038,725 A | 8/1977 | Keefe |
| 4,103,690 A | 8/1978 | Harris |
| 4,140,125 A | 2/1979 | Smith |
| 4,170,990 A | 10/1979 | Baumgart et al. |
| 4,192,315 A | 3/1980 | Hilzinger et al. |
| 4,217,902 A | 8/1980 | March |
| 4,324,248 A | 4/1982 | Perlin |
| 4,345,601 A | 8/1982 | Fukuda |
| 4,416,266 A | 11/1983 | Baucom |
| 4,456,017 A | 6/1984 | Miles |
| 4,485,816 A | 12/1984 | Krumme |
| 4,522,207 A | 6/1985 | Klieman et al. |
| 4,535,764 A | 8/1985 | Ebert |
| 4,548,202 A | 10/1985 | Duncan |
| 4,549,545 A | 10/1985 | Levy |
| 4,586,502 A | 5/1986 | Bedi et al. |
| 4,586,503 A | 5/1986 | Kirsch et al. |
| 4,595,007 A | 6/1986 | Mericle |
| 4,612,932 A | 9/1986 | Caspar et al. |
| 4,637,380 A | 1/1987 | Orejola |
| 4,665,906 A | 5/1987 | Jervis |
| 4,683,895 A | 8/1987 | Pohndorf |
| 4,705,040 A | 11/1987 | Mueller et al. |
| 4,719,924 A | 1/1988 | Crittenden et al. |
| 4,730,615 A | 3/1988 | Sutherland et al. |
| 4,741,330 A | 5/1988 | Hayhurst |
| 4,743,253 A | 5/1988 | Magladry |
| 4,750,492 A | 6/1988 | Jacobs |
| 4,809,695 A | 3/1989 | Gwathmey et al. |
| 4,823,794 A | 4/1989 | Pierce |
| 4,863,460 A | 9/1989 | Magladry |
| 4,873,975 A | 10/1989 | Walsh et al. |
| 4,896,668 A | 1/1990 | Popoff et al. |
| 4,899,744 A | 2/1990 | Fujitsuka et al. |
| 4,901,721 A | 2/1990 | Hakki |
| 4,924,866 A | 5/1990 | Yoon |
| 4,926,860 A | 5/1990 | Stice et al. |
| 4,929,240 A | 5/1990 | Kirsch et al. |
| 4,932,955 A | 6/1990 | Merz et al. |
| 4,950,283 A | 8/1990 | Dzubow et al. |
| 4,950,285 A | 8/1990 | Wilk |
| 4,955,913 A | 9/1990 | Robinson |
| 4,976,715 A | 12/1990 | Bays et al. |
| 4,983,176 A | 1/1991 | Cushman et al. |
| 4,990,152 A | 2/1991 | Yoon |
| 4,997,439 A | 3/1991 | Chen |
| 5,002,550 A | 3/1991 | Li |
| 5,002,562 A | 3/1991 | Oberlander |
| 5,002,563 A | 3/1991 | Pyka et al. |
| 5,026,379 A | 6/1991 | Yoon |
| 5,047,047 A | 9/1991 | Yoon |
| 5,053,047 A | 10/1991 | Yoon |
| 5,070,805 A | 12/1991 | Plante |
| 5,071,431 A | 12/1991 | Sauter et al. |
| 5,074,874 A | 12/1991 | Yoon et al. |
| 5,078,731 A | 1/1992 | Hayhurst |
| 5,100,418 A | 3/1992 | Yoon et al. |
| 5,116,840 A | 5/1992 | Ganguly et al. |
| 5,123,913 A | 6/1992 | Wilk et al. |
| RE34,021 E | 8/1992 | Mueller et al. |
| 5,152,769 A | 10/1992 | Baber |
| 5,154,189 A | 10/1992 | Oberlander |
| 5,158,566 A | 10/1992 | Pianetti |
| 5,163,954 A | 11/1992 | Curcio et al. |
| 5,171,250 A | 12/1992 | Yoon |
| 5,171,251 A | 12/1992 | Bregen et al. |
| 5,171,252 A | 12/1992 | Friedland |
| 5,174,087 A | 12/1992 | Bruno |
| 5,196,022 A | 3/1993 | Bilweis |
| 5,219,358 A | 6/1993 | Bendel et al. |
| 5,222,976 A | 6/1993 | Yoon |
| 5,234,449 A | 8/1993 | Bruker et al. |
| 5,236,440 A | 8/1993 | Hlavacek |
| 5,242,456 A | 9/1993 | Nash et al. |
| 5,246,443 A | 9/1993 | Mai |
| 5,258,011 A | 11/1993 | Drews |
| 5,258,015 A | 11/1993 | Li et al. |
| 5,269,783 A | 12/1993 | Sander |
| 5,269,809 A | 12/1993 | Hayhurst et al. |
| 5,282,832 A | 2/1994 | Toso et al. |
| 5,290,289 A | 3/1994 | Sanders et al. |
| 5,304,204 A | 4/1994 | Bregen |
| 5,306,290 A | 4/1994 | Martins et al. |
| 5,306,296 A | 4/1994 | Wright et al. |
| 5,312,436 A | 5/1994 | Coffey et al. |
| 5,330,503 A | 7/1994 | Yoon |
| 5,336,239 A | 8/1994 | Gimpelson |
| 5,356,424 A | 10/1994 | Buzerak et al. |
| 5,374,268 A | 12/1994 | Sander |
| 5,383,904 A | 1/1995 | Totakura et al. |
| 5,383,905 A | 1/1995 | Golds et al. |
| 5,391,173 A | 2/1995 | Wilk |
| 5,403,346 A | 4/1995 | Loeser |
| 5,409,499 A | 4/1995 | Yi |
| 5,437,680 A | 8/1995 | Yoon |
| 5,437,685 A | 8/1995 | Blasnik |
| 5,439,479 A | 8/1995 | Shichman et al. |
| 5,445,167 A | 8/1995 | Yoon et al. |
| 5,450,860 A | 9/1995 | O'Connor |
| 5,452,733 A | 9/1995 | Sterman et al. |

(56) References Cited

U.S. PATENT DOCUMENTS

| | | |
|---|---|---|
| 5,456,246 A | 10/1995 | Schmieding et al. |
| 5,462,561 A | 10/1995 | Voda |
| 5,474,557 A | 12/1995 | Mai |
| 5,474,572 A | 12/1995 | Hayhurst |
| 5,480,405 A | 1/1996 | Yoon |
| 5,486,197 A | 1/1996 | Le et al. |
| 5,496,336 A | 3/1996 | Cosgrove et al. |
| 5,499,990 A | 3/1996 | Schulken et al. |
| 5,500,000 A | 3/1996 | Feagin et al. |
| 5,520,691 A | 5/1996 | Branch |
| 5,520,702 A | 5/1996 | Sauer et al. |
| 5,527,342 A | 6/1996 | Pietrzak et al. |
| 5,531,763 A | 7/1996 | Mastri et al. |
| 5,545,178 A | 8/1996 | Kensey et al. |
| 5,549,619 A | 8/1996 | Peters et al. |
| 5,562,685 A | 10/1996 | Mollenauer et al. |
| 5,569,274 A | 10/1996 | Rapacki et al. |
| 5,569,301 A | 10/1996 | Granger et al. |
| 5,582,616 A | 12/1996 | Bolduc et al. |
| 5,582,619 A | 12/1996 | Ken |
| 5,586,983 A | 12/1996 | Sanders et al. |
| 5,591,179 A | 1/1997 | Edelstein |
| 5,593,414 A | 1/1997 | Shipp et al. |
| 5,593,424 A | 1/1997 | Northrup, III |
| 5,609,608 A | 3/1997 | Benett et al. |
| 5,626,590 A | 5/1997 | Wilk |
| 5,630,824 A | 5/1997 | Hart |
| 5,632,752 A | 5/1997 | Buelna |
| 5,632,753 A | 5/1997 | Loeser |
| 5,643,289 A | 7/1997 | Sauer et al. |
| 5,643,295 A | 7/1997 | Yoon |
| 5,645,553 A | 7/1997 | Kolesa et al. |
| 5,645,568 A | 7/1997 | Chervitz et al. |
| 5,665,109 A | 9/1997 | Yoon |
| 5,669,917 A | 9/1997 | Sauer et al. |
| 5,669,935 A | 9/1997 | Rosenman et al. |
| 5,681,351 A | 10/1997 | Jamiolkowski et al. |
| 5,683,417 A | 11/1997 | Cooper |
| 5,695,505 A | 12/1997 | Yoon |
| 5,697,943 A | 12/1997 | Sauer et al. |
| 5,700,270 A | 12/1997 | Peyser et al. |
| 5,700,271 A | 12/1997 | Whitfield et al. |
| 5,707,380 A | 1/1998 | Hinchliffe et al. |
| 5,709,693 A | 1/1998 | Taylor |
| 5,709,695 A | 1/1998 | Northrup, III |
| 5,725,539 A | 3/1998 | Matern |
| 5,725,542 A | 3/1998 | Yoon |
| 5,725,556 A | 3/1998 | Moser et al. |
| 5,728,135 A | 3/1998 | Bregen et al. |
| 5,735,290 A | 4/1998 | Sterman et al. |
| 5,735,877 A | 4/1998 | Pagedas |
| 5,766,183 A | 6/1998 | Sauer |
| 5,776,188 A | 7/1998 | Shepherd et al. |
| 5,799,661 A | 9/1998 | Boyd et al. |
| 5,810,851 A | 9/1998 | Yoon |
| 5,810,882 A | 9/1998 | Bolduc et al. |
| 5,820,631 A | 10/1998 | Nobles |
| 5,824,008 A | 10/1998 | Bolduc et al. |
| 5,830,221 A | 11/1998 | Stein et al. |
| 5,833,696 A | 11/1998 | Whitfield et al. |
| 5,845,645 A | 12/1998 | Bonutti |
| 5,849,019 A | 12/1998 | Yoon |
| 5,861,004 A | 1/1999 | Kensey et al. |
| 5,879,371 A | 3/1999 | Gardiner et al. |
| 5,891,130 A | 4/1999 | Palermo et al. |
| 5,891,160 A | 4/1999 | Williamson, IV et al. |
| 5,895,393 A | 4/1999 | Pagedas |
| 5,895,394 A | 4/1999 | Kienzle et al. |
| 5,919,207 A | 7/1999 | Taheri |
| 5,948,001 A | 9/1999 | Larsen |
| 5,961,481 A | 10/1999 | Sterman et al. |
| 5,961,539 A | 10/1999 | Northrup, III et al. |
| 5,964,772 A | 10/1999 | Bolduc et al. |
| 5,972,024 A | 10/1999 | Northrup, III et al. |
| 5,976,159 A | 11/1999 | Bolduc et al. |
| 5,984,917 A | 11/1999 | Fleischman et al. |
| 5,989,242 A | 11/1999 | Saadat et al. |
| 5,989,268 A | 11/1999 | Pugsley, Jr. et al. |
| 5,997,556 A | 12/1999 | Tanner |
| 6,001,110 A | 12/1999 | Adams |
| 6,013,084 A | 1/2000 | Ken et al. |
| 6,015,428 A | 1/2000 | Pagedas |
| 6,039,176 A | 3/2000 | Wright |
| 6,066,160 A | 5/2000 | Colvin et al. |
| 6,074,409 A | 6/2000 | Goldfarb |
| 6,120,524 A | 9/2000 | Taheri |
| 6,132,438 A | 10/2000 | Fleischman et al. |
| 6,139,540 A | 10/2000 | Rost et al. |
| 6,143,004 A | 11/2000 | Davis et al. |
| 6,176,413 B1 | 1/2001 | Heck et al. |
| 6,190,373 B1 | 2/2001 | Palermo et al. |
| 6,193,733 B1 | 2/2001 | Adams |
| 6,193,734 B1 | 2/2001 | Bolduc et al. |
| 6,231,592 B1 | 5/2001 | Bonutti et al. |
| 6,241,765 B1 | 6/2001 | Griffin et al. |
| 6,254,615 B1 | 7/2001 | Bolduc et al. |
| 6,306,141 B1 | 10/2001 | Jervis |
| 6,346,112 B2 | 2/2002 | Adams |
| 6,368,334 B1 | 4/2002 | Sauer |
| 6,432,123 B2 | 8/2002 | Schwartz et al. |
| 6,475,230 B1 | 11/2002 | Bonutti et al. |
| 6,514,265 B2 | 2/2003 | Ho et al. |
| 6,533,796 B1 | 3/2003 | Sauer et al. |
| 6,537,290 B2 | 3/2003 | Adams et al. |
| 6,551,332 B1 | 4/2003 | Nguyen et al. |
| 6,589,279 B1 | 7/2003 | Anderson et al. |
| 6,607,541 B1 | 8/2003 | Gardiner et al. |
| 6,613,059 B2 | 9/2003 | Schaller et al. |
| 6,626,930 B1 | 9/2003 | Allen et al. |
| 6,641,592 B1 | 11/2003 | Sauer et al. |
| 6,641,593 B1 | 11/2003 | Schaller et al. |
| 6,682,540 B1 | 1/2004 | Sancoff et al. |
| 6,719,767 B1 | 4/2004 | Kimblad |
| 6,746,457 B2 | 6/2004 | Dana et al. |
| 6,749,622 B2 | 6/2004 | McGuckin, Jr. et al. |
| 6,776,784 B2 | 8/2004 | Ginn |
| 6,860,890 B2 | 3/2005 | Bachman et al. |
| 6,896,686 B2 | 5/2005 | Weber |
| 6,913,607 B2 | 7/2005 | Ainsworth et al. |
| 6,918,917 B1 | 7/2005 | Nguyen et al. |
| 6,921,407 B2 | 7/2005 | Nguyen et al. |
| 6,926,730 B1 | 8/2005 | Nguyen et al. |
| 6,945,980 B2 | 9/2005 | Nguyen et al. |
| 6,960,221 B2 | 11/2005 | Ho et al. |
| 7,011,669 B2 | 3/2006 | Kimblad |
| 7,083,628 B2 | 8/2006 | Bachman |
| 7,094,244 B2 | 8/2006 | Schreck |
| 7,112,207 B2 | 9/2006 | Allen et al. |
| 7,220,266 B2 | 5/2007 | Gambale |
| 7,235,086 B2 | 6/2007 | Sauer et al. |
| 7,264,625 B1 | 9/2007 | Buncke |
| 7,381,210 B2 | 6/2008 | Zarbatany et al. |
| 7,628,797 B2 | 12/2009 | Tieu et al. |
| 7,731,727 B2 | 6/2010 | Sauer |
| 7,833,237 B2 * | 11/2010 | Sauer ............... A61B 17/0485 606/148 |
| 7,842,051 B2 | 11/2010 | Dana et al. |
| 7,862,584 B2 | 1/2011 | Lyons et al. |
| 7,875,056 B2 | 1/2011 | Jervis et al. |
| 7,959,674 B2 | 6/2011 | Shu et al. |
| 7,981,139 B2 | 7/2011 | Martin et al. |
| 8,021,421 B2 | 9/2011 | Fogarty et al. |
| 8,100,923 B2 | 1/2012 | Paraschac et al. |
| 8,105,355 B2 | 1/2012 | Page et al. |
| 8,252,005 B2 * | 8/2012 | Findlay, III ........ A61B 17/0487 606/139 |
| 8,398,657 B2 | 3/2013 | Sauer |
| 8,398,680 B2 | 3/2013 | Sauer et al. |
| 8,425,555 B2 | 4/2013 | Page et al. |
| 8,480,686 B2 | 7/2013 | Bakos et al. |
| 8,753,373 B2 | 6/2014 | Chau et al. |
| 9,017,347 B2 | 4/2015 | Oba et al. |
| 2003/0109922 A1 | 6/2003 | Peterson et al. |
| 2003/0195563 A1 | 10/2003 | Foerster |

(56) References Cited

U.S. PATENT DOCUMENTS

| | | |
|---|---|---|
| 2003/0233105 A1* | 12/2003 | Gayton .............. A61B 17/0684 606/142 |
| 2004/0181238 A1 | 9/2004 | Zarbatany et al. |
| 2004/0204724 A1 | 10/2004 | Kissel et al. |
| 2004/0249414 A1 | 12/2004 | Kissel et al. |
| 2005/0251209 A1 | 11/2005 | Saadat et al. |
| 2006/0047314 A1 | 3/2006 | Green |
| 2006/0079913 A1 | 4/2006 | Whitfield et al. |
| 2006/0089571 A1 | 4/2006 | Gertner |
| 2006/0184203 A1 | 8/2006 | Martin et al. |
| 2006/0265010 A1 | 11/2006 | Paraschac et al. |
| 2006/0276871 A1 | 12/2006 | Lamson et al. |
| 2007/0005079 A1 | 1/2007 | Zarbatany et al. |
| 2007/0005081 A1 | 1/2007 | Findlay et al. |
| 2007/0049952 A1 | 3/2007 | Weiss |
| 2007/0049970 A1 | 3/2007 | Belef et al. |
| 2007/0088391 A1 | 4/2007 | McAlexander et al. |
| 2007/0179530 A1* | 8/2007 | Tieu ................... A61B 17/0487 606/232 |
| 2007/0270907 A1 | 11/2007 | Stokes et al. |
| 2008/0154286 A1 | 6/2008 | Abbott et al. |
| 2008/0255591 A1 | 10/2008 | Harada et al. |
| 2008/0281356 A1 | 11/2008 | Chau et al. |
| 2009/0143821 A1 | 6/2009 | Stupak |
| 2010/0001038 A1 | 1/2010 | Levin et al. |
| 2010/0076462 A1 | 3/2010 | Bakos et al. |
| 2010/0324597 A1* | 12/2010 | Shikhman .......... A61B 17/0467 606/232 |
| 2011/0087241 A1 | 4/2011 | Nguyen |
| 2011/0087242 A1 | 4/2011 | Pribanic et al. |
| 2011/0224714 A1 | 9/2011 | Gertner |
| 2011/0283514 A1 | 11/2011 | Fogarty et al. |
| 2012/0089182 A1 | 4/2012 | Page et al. |
| 2013/0110164 A1 | 5/2013 | Milazzo et al. |
| 2013/0158600 A1 | 6/2013 | Conklin et al. |
| 2014/0031864 A1 | 1/2014 | Jafari et al. |

FOREIGN PATENT DOCUMENTS

| | | |
|---|---|---|
| DE | 69512446 T2 | 5/2000 |
| DE | 69612447 T2 | 7/2001 |
| EP | 0669101 A1 | 8/1995 |
| EP | 0669103 A1 | 8/1995 |
| EP | 1484023 A1 | 12/2004 |
| WO | 0166001 A2 | 9/2001 |

OTHER PUBLICATIONS

International Search Report for PCT/US2014/046423, dated Oct. 20, 2014.

EP Supplementary Search Report for EP12858766, completed Sep. 7, 2015.

CN Office Action for App No. 2012800690769, dated Mar. 23, 2015.

European Supplementary Search Report dated Feb. 9, 2016 for EP13817447.

Int'l. Search Report for PCT/US15/065033, dated Feb. 18, 2016.

* cited by examiner

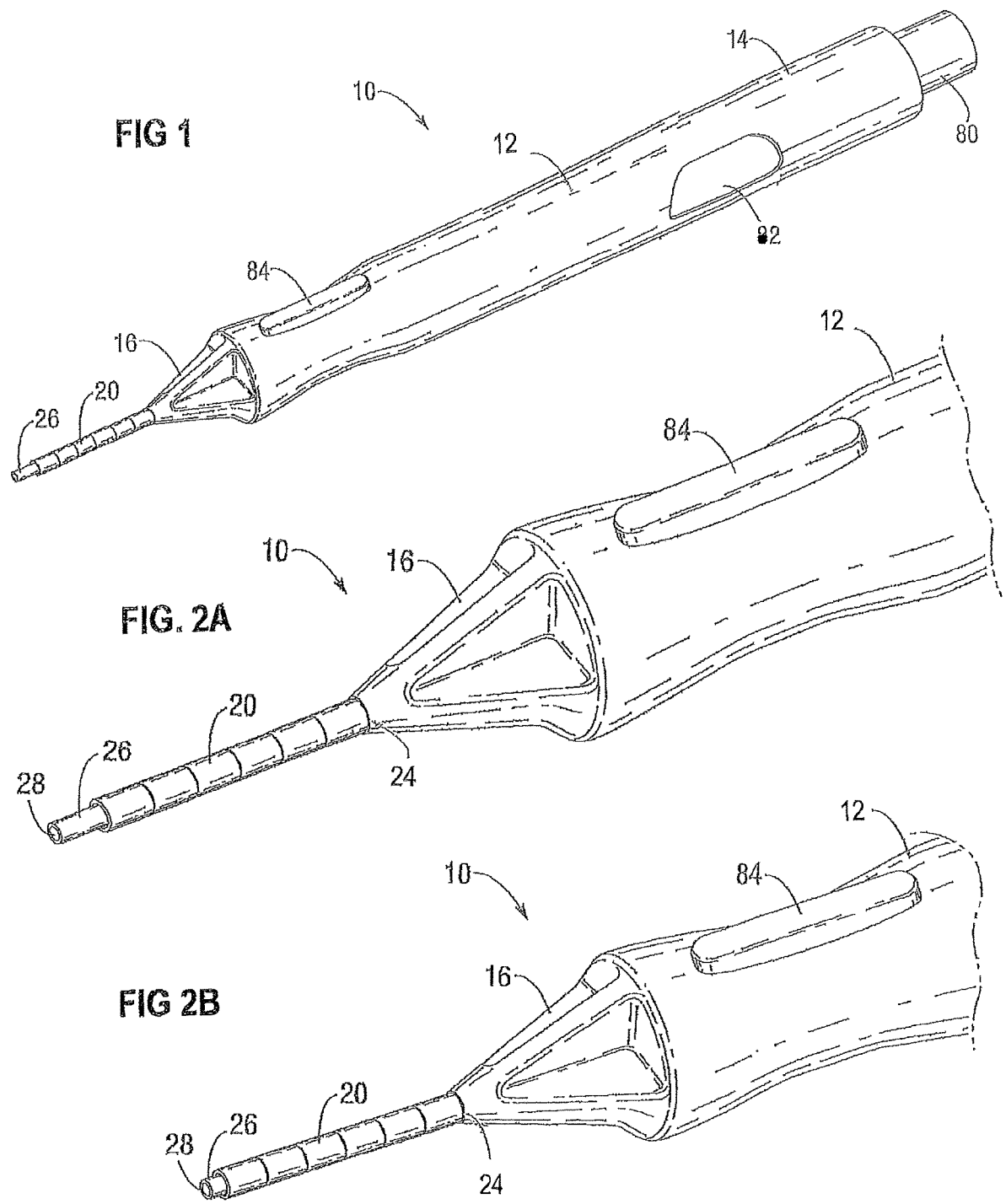

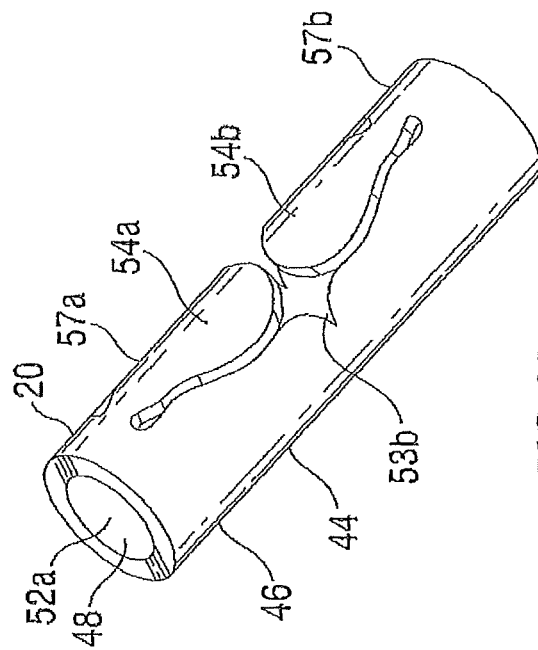
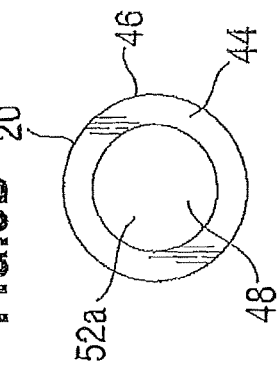
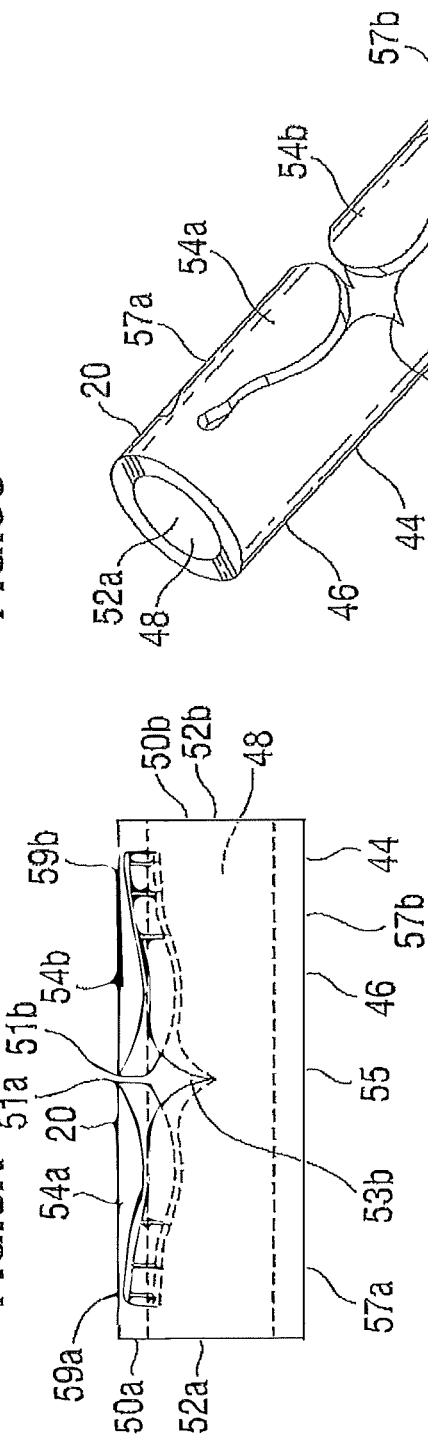
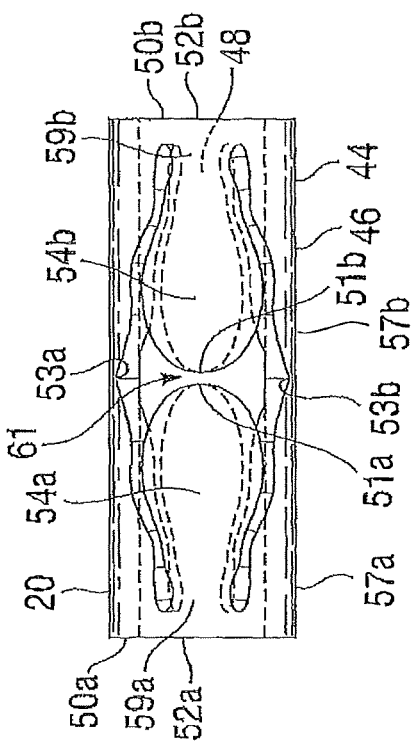

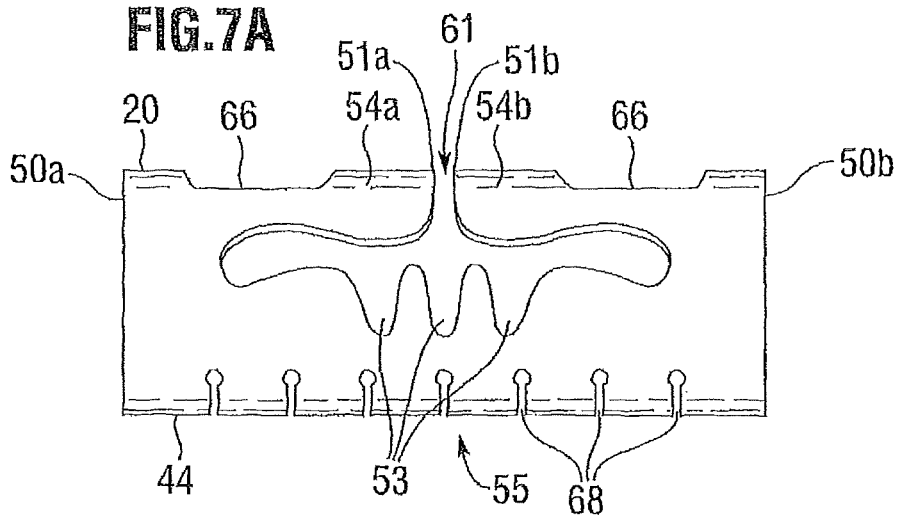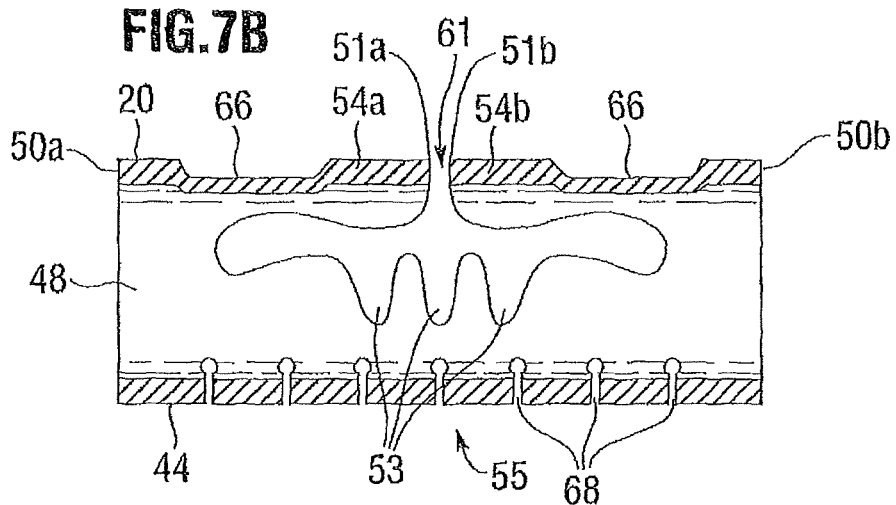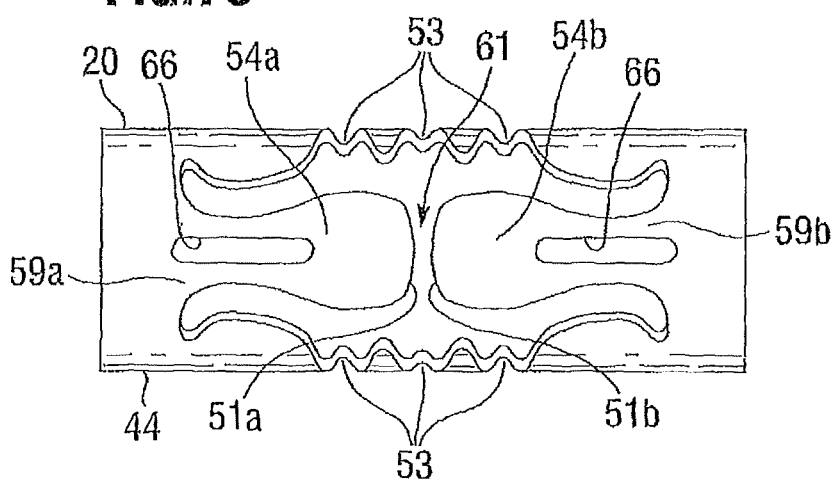

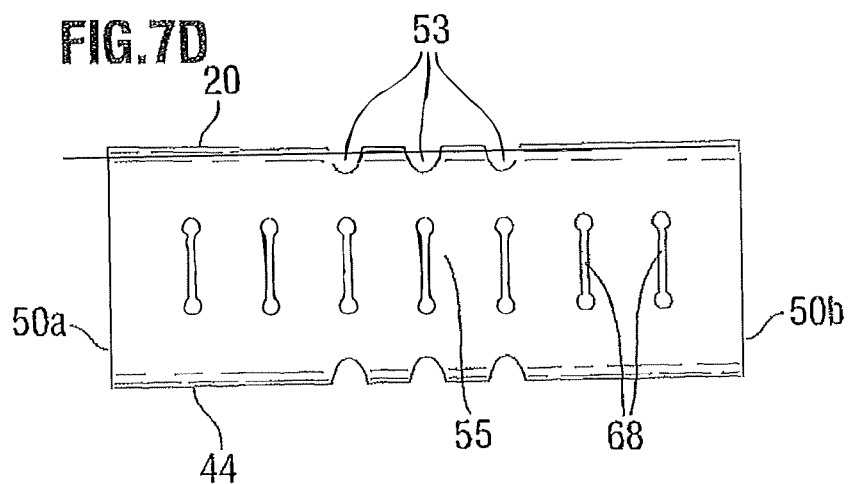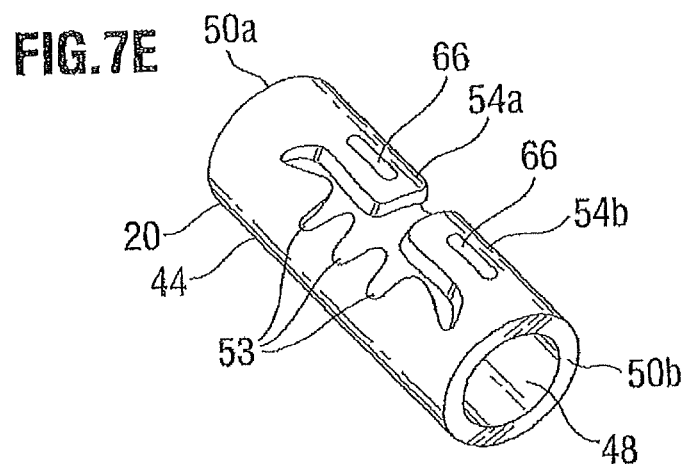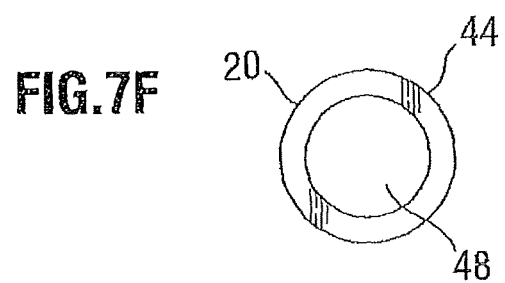

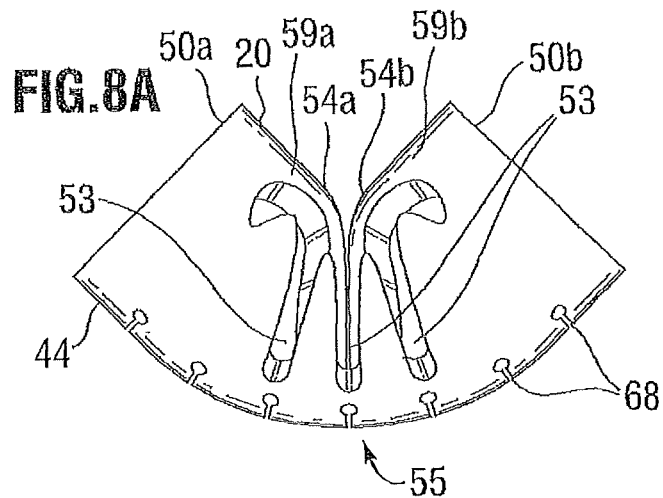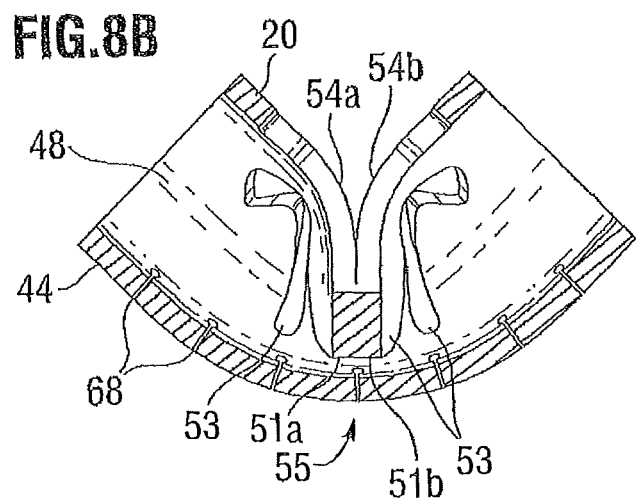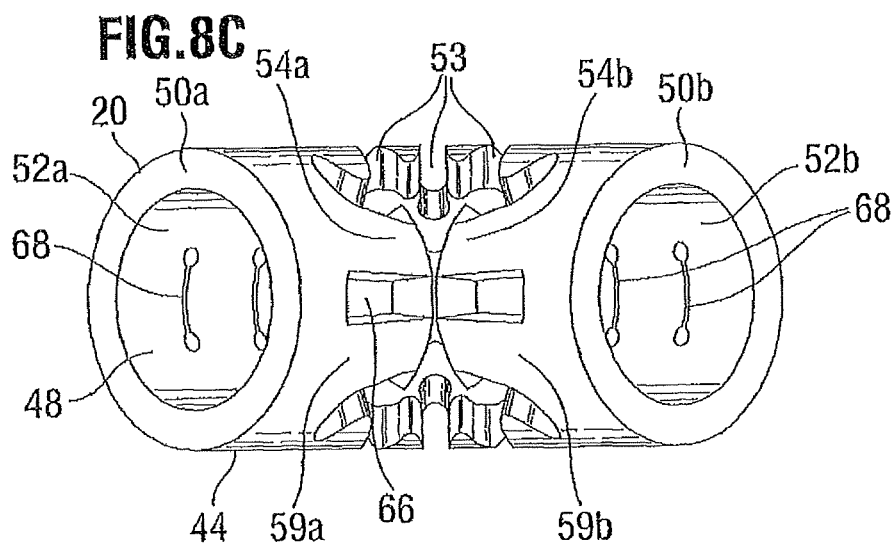

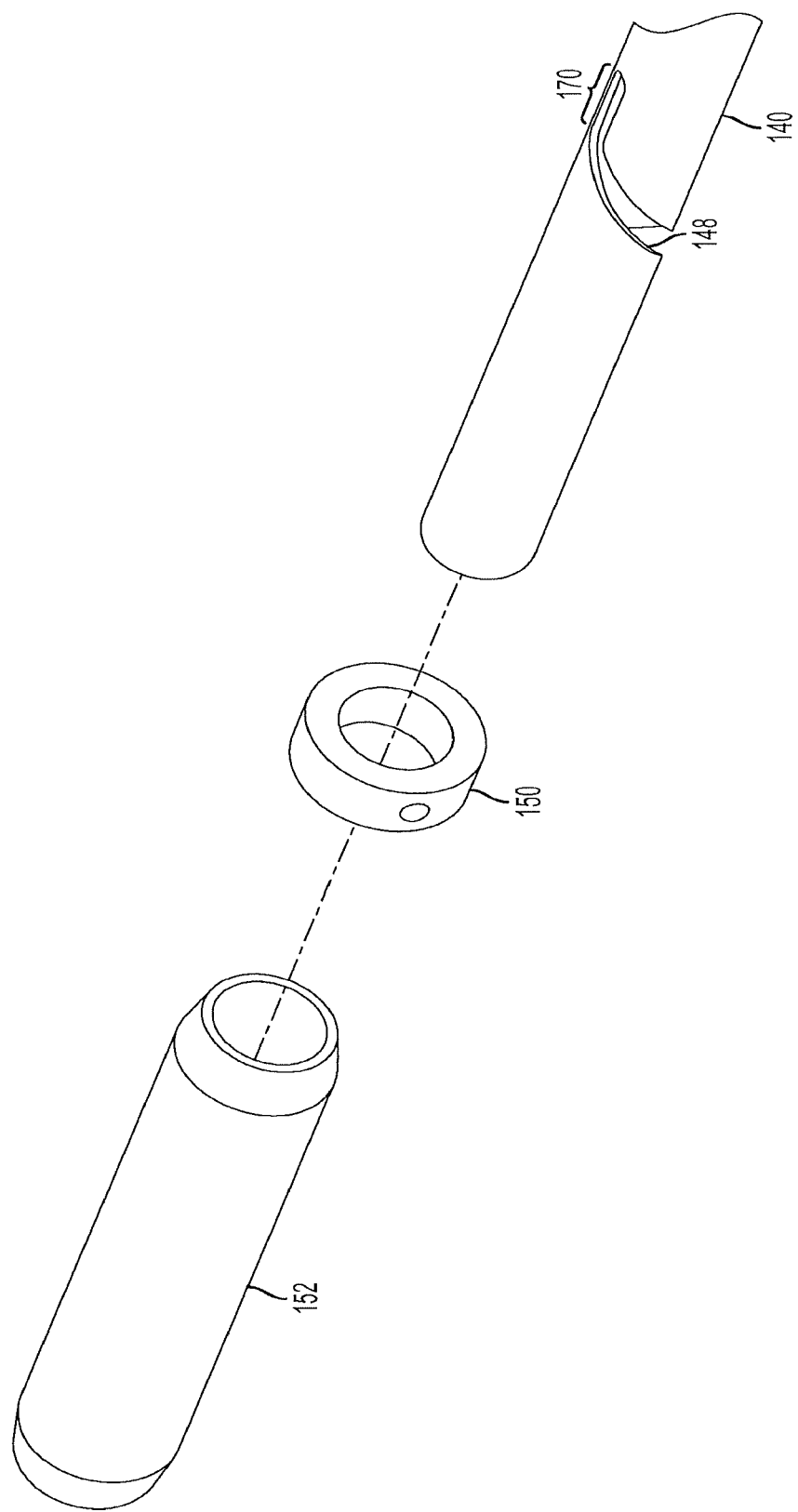

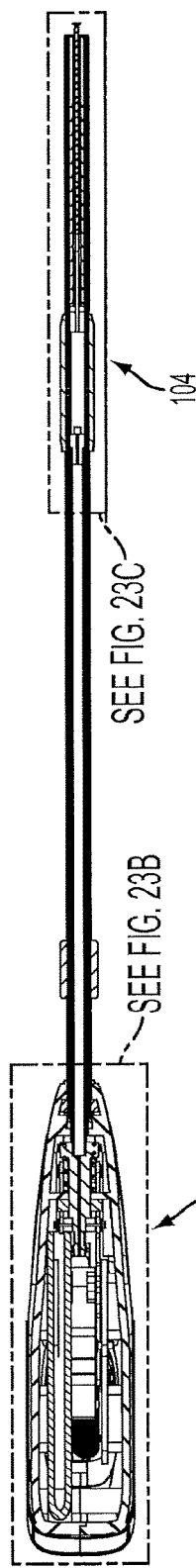
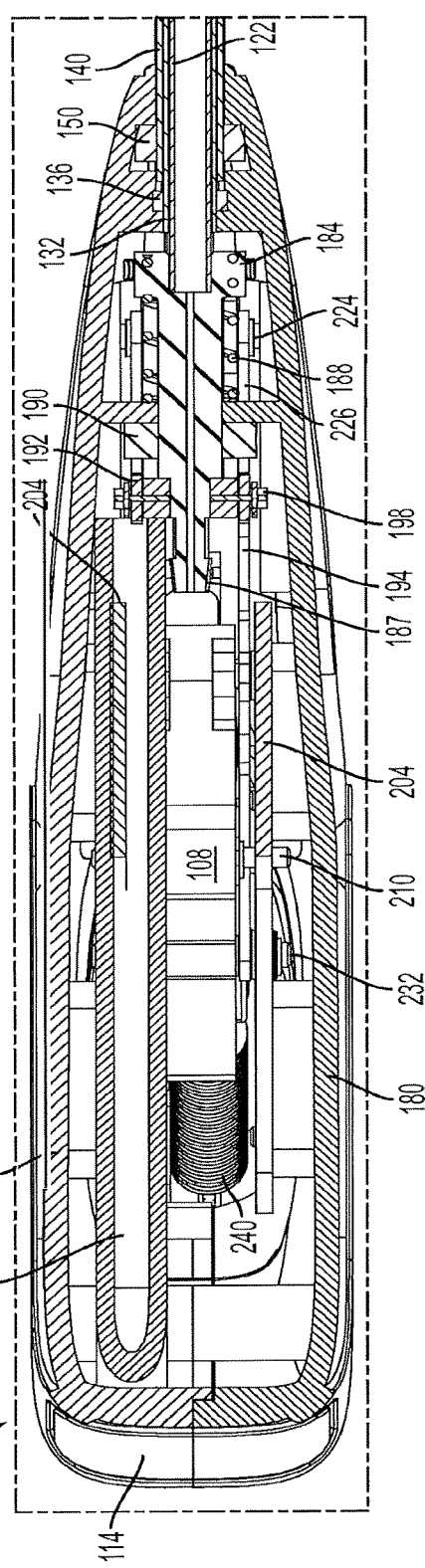
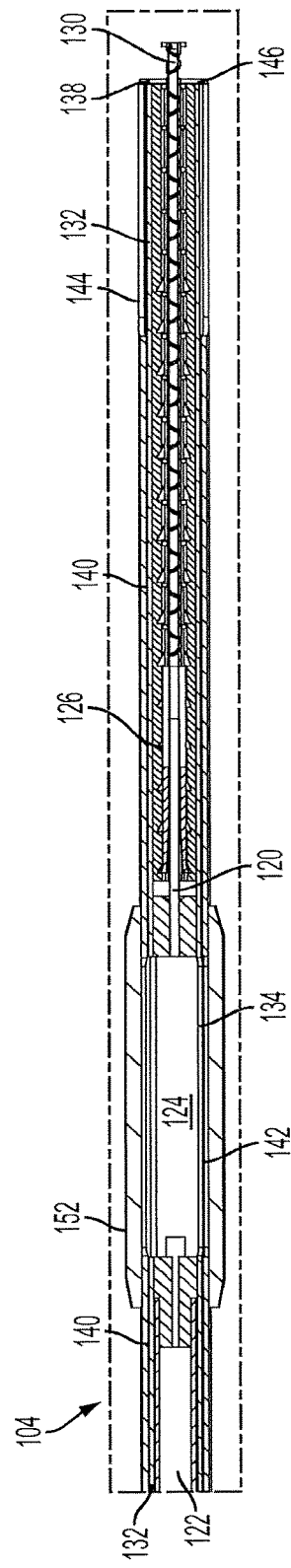
FIG. 23A
FIG. 23B
FIG. 23C

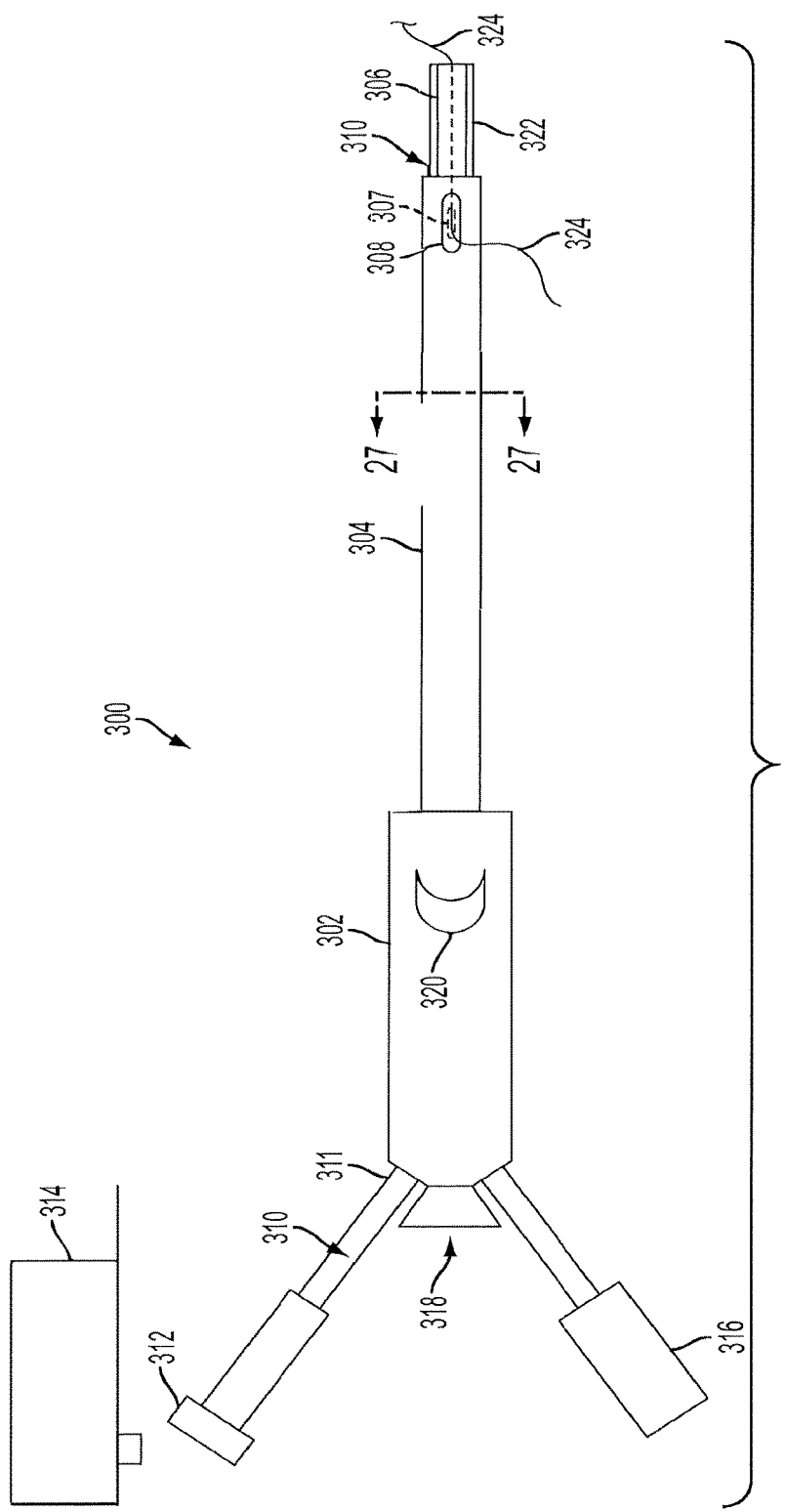
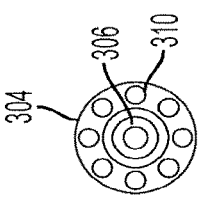
FIG. 26
FIG. 27

SUTURE CLIP DEPLOYMENT DEVICES

CROSS-REFERENCE TO RELATED APPLICATIONS

This application is a divisional of U.S. patent application Ser. No. 15/385,203, filed Dec. 20, 2016, now U.S. Pat. No. 10,314,573, which is a continuation of U.S. patent application Ser. No. 14/658,575, filed Mar. 16, 2015, now U.S. Pat. No. 9,549,730, which is a continuation of U.S. patent application Ser. No. 13/715,640, filed Dec. 14, 2012, now U.S. Pat. No. 9,017,347, which claims the benefit of U.S. Patent Application No. 61/579,497, filed Dec. 22, 2011, the disclosures all of which are incorporated by reference herein in their entireties.

FIELD

This disclosure relates to devices and methods for securing sutures using clips.

BACKGROUND

Sutures are used for a variety of surgical purposes, such as approximation of tissue and ligation of tissue. When placing sutures, the strand of suture material to be used typically has a needle affixed to one end which is passed (looped) through the tissue to be approximated or ligated, forming a stitch. The stitch is then tensioned appropriately, and the two free ends of the suture loop, the needle end and the non-needle end, are knotted to retain the desired tension in the stitch. Forming knots in suture during open surgery is a simple matter, though time-consuming, but forming knots in sutures during endoscopic surgery can require two surgeons to cooperate in a multi-step process which is performed with multiple instruments to pass the needle and suture back and forth to tie the suture knot.

Suture locking devices that eliminate the need to tie knots in order to speed up heart valve replacement are known, as are suture locking devices in general. Suture retainers or locks are used in place of suture knots to prevent passage of a suture end into and through tissue and to maintain the tension applied to the suture material during the suturing procedure.

When using a method that employs a clip to secure the suture, the clip can be delivered by advancing the clip along a suture line to the area of interest, and then deploying the clip such that the clip secures the suture in place. With the clip thus secured, the excess suture can be cut and removed from the patient. An example of such a clip as well as methods and devices for use therewith are disclosed in U.S. Patent Pub. No. 2007/0005081 and U.S. Pat. No. 7,628,797, the entire contents of which are expressly incorporated herein by reference.

Despite the existence of knotless suture locking devices in the art, there is a need for improved devices that enable easy access to the suture, accurate tensioning of the suture and are simple to use. In light of the foregoing, there is presently a need for improved systems for securing sutures with clips.

SUMMARY

Disclosed herein are improved suture clip delivery devices and systems that are especially useful for securing heart valve repair or replacement prostheses in or near the heart. The devices and methods are particularly well suited for traditional surgery or minimally invasive surgery. The devices disclosed herein can eliminate the need for surgical knots thus reducing surgical time and exposure. Further, the devices can improve the ease of implantation because the clinician need not tie knots in the limited space in and around the heart.

Some embodiments of suture clip delivery systems described herein utilize a suture clip having a generally tubular shape, with an inner lumen passing through the tube and a handheld vacuum-assisted device for deploying the suture clips. The inner lumen of the device and clip is sized and configured so that one or more lines of suture may pass therethrough. The clip has an open configuration wherein the inner lumen is generally unobstructed, and a closed configuration wherein the inner lumen is at least partially obstructed so that suture line(s) passing therethrough are prevented from moving in one or more directions.

An exemplary system disclosed herein includes a device having a generally tubular main body with a proximal end, a distal end, a vacuum port located at the distal end, a hollow inner body longitudinally slidable within the main body and extending from the main body at its distal end, a suture recess located in the generally tubular main body, and at least one suture clip configured to frictionally fit on an outer surface of the inner body. The main body further comprises a mechanical advancer button and clip deployment occurs when the device is mechanically actuated via the mechanical advancer button. Multiple clips can be loaded onto the inner body for deployment. The clips are preferably made of a shape memory material.

Also disclosed herein is are methods for anchoring an implant to soft tissue, the implant having been advanced to the soft tissue down a plurality of suture lines, comprising providing a delivery device having a generally tubular main body with a proximal end, a distal end, a vacuum port located at the distal end, an inner body longitudinally slidable within the main body and extending from the main body at its distal end, a suture recess located in the generally tubular main body, and at least one suture clip configured to frictionally fit on an outer surface of the inner body; connecting a vacuum source to the vacuum port; approaching the suture lines with a distal end of the inner body of the device; applying a vacuum so as to draw the suture lines into the distal end of the delivery device and through the main body; retrieving the suture lines through the suture recess; adjusting tension in the suture lines; and actuating the device so as to force the suture clip off the inner body and onto the suture lines so as to lock the suture lines in place.

Some disclosed devices for deploying a suture clip onto a suture comprise a proximal handle portion comprising an actuation mechanism and a generally tubular main shaft having an inner lumen, a proximal end portion coupled to the actuation mechanism, a distal end portion having a distal opening in communication with the inner lumen, and an intermediate portion having a radial opening in communication with the inner lumen. The main shaft is configured to hold one or more annular suture clips loaded on the distal end portion of the main shaft and the main shaft is also configured to receive at least one suture extending through the distal opening, through the inner lumen, and through the radial opening. The device further comprises a pusher positioned at least partially around the main shaft and coupled to the actuation mechanism independently of the main shaft. The pusher is configured to be positioned proximal to the one or more suture clips when the one or more suture clips are loaded on the main shaft. The actuation mechanism is configured to cause the main shaft to move proximally relative to the handle portion, the pusher, and the one or more suture clips loaded on the main shaft, such that a distal-most one of the one or more suture slips slides distally off of a distal end of the main shaft and onto a suture extending through the distal opening of the main shaft.

In some embodiments, the inner lumen of the main shaft is fluidly couplable to a vacuum source that reduce pressure within the inner lumen such that a suture can be drawn into the inner lumen through the distal opening of the main shaft.

In some embodiment, the handle portion comprises a vacuum source that is fluidly coupled the inner lumen of the main shaft to assist in drawing a suture through the distal opening and into the inner lumen. The handle portion can further comprise a manual vacuum controller that controls the vacuum in the inner lumen.

In some embodiments, the device is configured such that, after a suture clip is deployed onto the suture, the actuation mechanism causes the main shaft, the pusher, and any suture clips remaining on the main shaft to move distally together relative to the handle portion.

Some embodiments further comprise an outer shaft positioned around the main shaft and the pusher and coupled to the handle portion. The outer shaft comprises a blade at a distal end portion that is configured to cut the suture after the suture clip is deployed onto the suture. The cutting of the suture occurs between the distal end of the main shaft and a proximal end of the deployed suture.

In some embodiments, the actuation mechanism causes the outer shaft to rotate relative to the main shaft and the handle portion, and wherein the rotation of outer shaft causes the cutting of the suture.

Some embodiments further comprise a cover member slidably mounted over the radial opening of the main shaft, the cover member being configured to selectively open and close the radial opening of the main shaft.

In some embodiments, the pusher comprises a ratcheting mechanism that allows the pusher to slide distally relative to the main shaft but prevents the pusher from sliding proximally relative to the main shaft.

In some embodiments, the device is configured to be loaded with a plurality of suture clips that are deployable without reloading the device.

Some embodiments further comprise a suture tension monitoring system configured to determine and display the amount of tension in a suture positioned within the inner lumen of the main shaft.

Some embodiments further comprise a suture clip monitoring system configured to determine and display the number of suture clips that are currently loaded on the main shaft.

Some embodiments further comprise a lighting system configured to provide light near the distal end of the main shaft. The lighting system can comprise one or more light fibers that extend along the length of the main shaft and are configured to conduct light from a proximal light source to near the distal end of the main shaft.

Some embodiments further comprise a visual monitoring system configured to capture visual information from the near the distal end of the main shaft and transfer the captured visual information to a proximal visual display.

In some embodiments, the one or more suture clips are comprised of a shape-memory material, wherein the one or more suture clips are held in a resiliently deformed annular configuration when loaded onto the main shaft, and wherein the one or more suture clips resiliently return toward a natural collapsed configuration when deployed onto the suture, thereby becoming frictionally secured to the suture.

An exemplary method for deploying a suture clip onto a suture comprises causing a free end of at least one suture to enter into a distal end portion of an inner lumen of a main shaft of a suture clip deployment device, and then causing the main shaft to move proximally relative to a suture clip mounted around an outer surface of the main shaft such that the suture clip slides distally off of a distal end of the main shaft and onto the at least one suture such that the suture clip resiliently secures to the suture.

In some methods, inserting a free end of the suture into the distal end portion of the inner lumen comprises reducing the air pressure within the inner lumen in order to draw the free end of the suture into the inner lumen.

In some methods, inserting a free end of the suture into the distal end portion of the inner lumen comprises drawing the free end of the suture out of the inner lumen through a lateral opening in the main shaft.

Some methods further include applying tension to the free end of the suture projecting from the lateral opening.

Some methods further include causing a blade of the suture clip deployment device to cut off the free end of the suture after the suture clip is secured to the suture. Such methods can further include, after the suture is cut, causing the main shaft and suture clips remaining mounted on the main shaft to move distally relative to a handle portion of the suture clip deployment device. After the main shaft and suture clips remaining mounted on the main shaft to move distally relative to a handle portion, the method can include repeating process to deploy another suture clip onto another suture.

A further understanding of the features and advantages of the present invention will become apparent from a consideration of the following detailed description.

BRIEF DESCRIPTION OF THE DRAWINGS

FIG. 1 depicts a perspective view of a vacuum-assisted suture clip delivery device as described herein.

FIGS. 2A and 2B show perspective views of the distal portion of the device of FIG. 1.

FIGS. 3A, 3B, 3C, and 3D depict side, top, perspective, and distal end views, respectively, of a suture clip in an open configuration according to an embodiment of the invention.

FIGS. 7A-7F depict side (solid), side (cross section), top, bottom, perspective, and end views, respectively, of a suture clip in an open configuration according to an embodiment of the invention.

FIGS. 8A-8E depict side (solid), side (cross section), top, bottom, and perspective views, respectively, of the suture clip of FIGS. 7A-7F in a closed configuration.

FIGS. 18B-18F are enlarged views of portions of FIG. 18A.

FIG. 23A is a cross-sectional view of the device of FIG. 21 taken along section line B-B of FIG. 21.

FIGS. 23B-23F are enlarged views of portions of FIG. 23A.

FIG. 26 is schematic top view of another exemplary suture deployment device that includes a lighting system and a visual monitoring system.

FIG. 27 is a cross-sectional view of a shaft portion of the device of FIG. 26 taken along section line 27-27.

DETAILED DESCRIPTION

Figure 4:
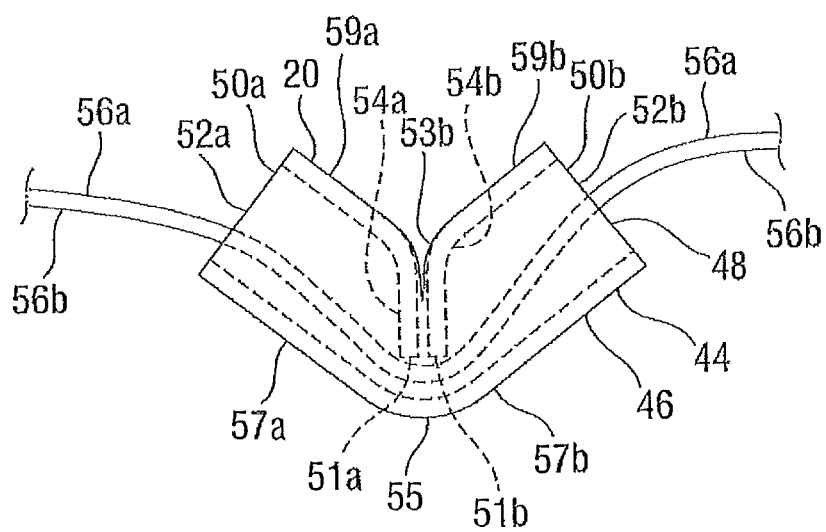
FIG. 4 depicts a side view of a suture clip in a closed configuration with a length of suture running therethrough according to an embodiment of the invention.

Described herein devices and methods for securing sutures with suture clips. FIG. 1 depicts a suture clip delivery device 10 according to one embodiment. The handheld suture clip delivery device 10 has a generally tubular main device body 12 having a proximal end 14 and a distal end 16. The proximal end 14 includes a vacuum port 80 and a suture recess 82. The distal end 16 includes a mechanical advancer button 84. Extending past the distal end 16 of the device is an inner body 26, shown here having multiple suture clips 20 positioned thereon. The inner body 26 is longitudinally slidably positioned within the main body 12 of the delivery device. The inner body 26 includes a distal end 28 which extends distally out of the main body distal opening 24. The vacuum port 80 located at the proximal end 14 of the device 12 is configured to be attached to a vacuum source (not shown). When the user attaches the vacuum port 80 to any vacuum source, suction is created within the device 10. The suction assists the user in drawing the suture lines into the distal end 28 of the inner body 26 thereby threading the sutures through the device. The suture lines exit the device 10 at the suture recess 82. It should be noted that the suture clip delivery device 10 can be manufactured in a variety of shapes, sizes, lengths, widths, and biologically-compatible materials as desired for a particular application.

The device 10 and the inner body 26 both feature at least one lumen to allow passage of a suture therethrough as well as to allow for suction via the vacuum port 80. Some embodiments may include more than one lumen within the device 10. For example, one lumen may extend from the distal end 28 of the inner body 26 to the vacuum port 80, and another separate lumen may extend from the distal end 28 of the inner body 26 to the suture recess 82. In either case, suction is used to draw the suture into the device 10; the ends of the sutures exit the device 10 via the suture recess 82 which enables the user to tension the sutures prior to clip deployment.

FIGS. 2A and 2B illustrate the distal portion of the suture clip delivery device 10. As shown, multiple clips 20 are loaded onto the outer surface of inner body 26 and are held onto the inner body 26 by a friction fit, thus preventing the clips 20 from inadvertently falling off the distal end 16 of the device 10 prior to deployment. The inner body 26 is slidably coupled within the main body of the device 12 to allow at least partial retraction of the inner body 26 into the distal end 16 of the device 10. FIG. 2A specifically shows the position of the inner body 26 relative to the clips 20 and distal end 16 of the device 10 prior to actuation using the mechanical advancer button 84. FIG. 2B shows the position of the inner body 26 relative to the clips 20 and distal end 16 of the device 10 after actuation. Actuation of the delivery device 10 using the advancer button 84 will be described in more detail below.

As can be seen in FIGS. 2A and 2B, the inner body 26 of the delivery device 10 is slidably positioned within main device body 12. A suture clip 20 is positioned on the inner body distal end 28, which protrudes from the main body distal opening 24. As depicted in FIG. 2B, the suture clip 20 is placed on inner member distal end 28 in its open configuration wherein the clip body is generally straight (i.e., unbent). The suture clip 20 is secured to the inner body distal end 28 by means of the frictional engagement of the clip body against the outer surface of inner body 26.

Note that a clip according to this particular invention may have a (relatively gentle) curve along its length but still be considered "generally straight." The term "generally straight" is used to refer to a configuration wherein the clip does not have a relatively tight bend sufficient to cause crimping of the inner lumen.

FIGS. 3A through 3D illustrate a suture clip 20 in an "open" configuration, while FIG. 4 depicts the suture clip 20 in a "closed" or "locked" configuration. The suture clip 20 can be manufactured from a variety of materials including, for example, nickel-titanium alloys, shape-memory alloys, stainless steel, titanium, various plastics, and other biologically-compatible materials. Suture clip 20 has a generally tubular body 44 and an outer wall 46, and includes a distal opening 50 leading to an internal attachment lumen 48 extending axially through the suture clip 20 to a proximal opening 52. The suture clip 20 includes one or more engagement tab(s) 54a, 54b formed in the suture clip 20 and configured to leave the inner lumen relatively unobstructed when in the "open" configuration as depicted in FIGS. 3A-3D, and to at least partially obstruct the inner lumen 48 when in a "closed" configuration, as depicted in FIG. 4. The suture clip 20 includes notches 53a, 53b formed adjacent the tabs 54a, 54b, with the notches 53a, 53b helping to create a hinge-point 55 about which the proximal half 57a and distal half 57b of the clip body 44 can bend.

The clip body 44, distal opening 50, proximal opening 52, inner lumen 48, and engagement tabs 54a, 54b are sized and configured (when the clip body 44 and engagement tabs 54a, 54b are in the "open" configuration as shown in FIGS. 3A-3D) to slidingly receive one or more suture leads therethrough. Prior to deployment, the clip body 44 is in its open (i.e., straightened) configuration, and the engagement tabs 54a, 54b are moved to their "open" configuration by being deflected radially out of the inner lumen 48 such that the engagement tabs 54a, 54b are essentially flush with the suture clip outer wall 46, thereby leaving the inner lumen 48 essentially unobstructed, or at least unobstructed to the extent necessary for the suture lines to slidingly pass within the lumen 48. As depicted in FIG. 3A, the inner lumen 48 (with the clip body 44 straightened and the engagement tabs 54a, 54b in their open configuration) provides a relatively large and unobstructed passage sufficient to permit suture leads to slide therethrough.

Upon deployment, i.e. after the suture leads have been retracted through the delivery device by means of a vacuum applied to the device, and tightened to their desired position, the suture clip 20 is advanced to its desired deployment position and forced off the end of the delivery device. The clip body 44 is bent (which may include stressing a plastically deformable clip to assume the bent configuration, or permitting a biased clip to spring back to the bent configuration), with clip bending occurring along a hinge point 55. The engagement tabs 54a, 54b are deflected or permitted to spring back into the inner lumen 48 toward the hinge point 55 such that the inner lumen 48 is at least partially blocked, as depicted in FIG. 4. Suture lines 56a, 56b are held fast within the closed clip 20, with the engagement tabs 54a, 54b engaging against and securing the suture lines 56a, 56b against the clip body 44. The "closed" engagement tabs 54a, 54b and bent clip body 44 cause the suture lines 56a, 56b passing therethrough to adopt a "serpentine" path through the clip inner lumen 48. This serpentine path, combined with the friction on the suture from the clip body 44 and engagement tabs 54a, 54b, serves to lock the suture 56a, 56b in place and prevent longitudinal movement thereof within the clip lumen 48. The suture 56a, 56b is thus held secure by the combination of tab 54a, 54b to clip inner wall interaction/forces and by the tortuous path that the bent clip body 44 and tabs 54a, 54b force the suture lines 56a, 56b to follow, which provides more surface area contact with the suture 56a, 56b to increase retention. Note also that the bending of the clip body 44 holds the tabs 54a, 54b against each other, so that neither of the tabs 54a, 54b can bend back outwardly without engaging against the other tab.

As shown in FIG. 4, the suture lines 56a, 56b are relatively thin as compared to the clip lumen 48. However, depending on the particular application, suture that is of a much greater thickness can be used with a clip according to the invention. If used with thicker suture(s), a clip 20, and particularly the tabs 54a, 54b, might assume a somewhat different shape once deployed. With a thicker suture line or lines, the tabs 54a, 54b would each be forced back outward (i.e., toward their "open" configuration") by the suture, but the bending of the clip body 44 and the resulting interaction between the tabs 54a, 54b will prevent excessive tab movement, and the suture will still be held securely within the clip body 44.

Depending on the particular embodiment, including the materials from which a particular suture clip is made, the clip body (and the bend therein) as well as the engagement tab(s) may be biased to spring toward a desired position, which may be either the closed configuration or the open configuration, depending on the particular application.

Figure 5A:
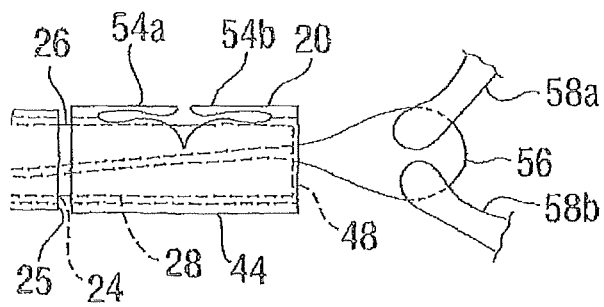
FIGS. 5A-5C depict side views of the most distal portion of the delivery device showing suture clip deployment according to an embodiment of the invention.
Figure 5B:
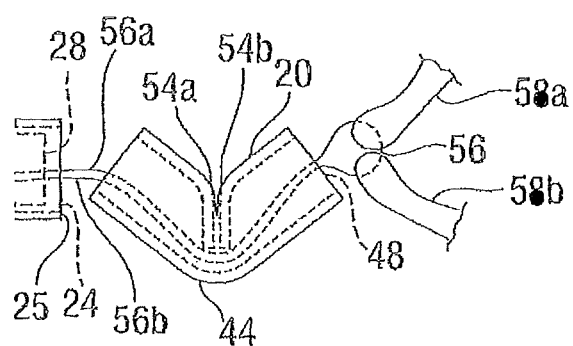
Figure 5C:
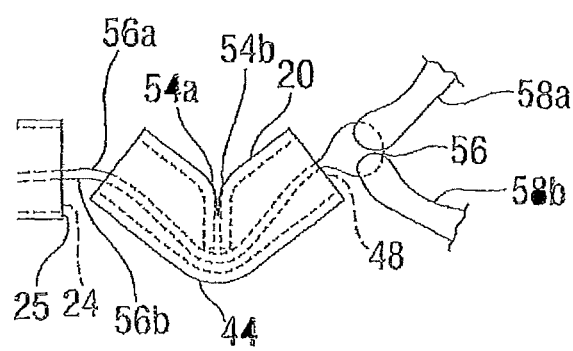

FIGS. 5A-5C depict, in various configurations, deployment of a clip 20 from the distal end 16 of the suture clip delivery device 10 according to an embodiment of the invention. FIG. 5A depicts the device inner body distal end 28 extending from device main body distal opening 24, with a suture clip 20 positioned on the inner body distal end 28. A suture line 56 extends through material or tissue portions 58a, 58b and vacuum is used to draw the suture line into the distal end of the device. In the particular embodiment depicted, the clip 20 is biased towards its closed configuration, and the inner body distal end 28 of the device 10 physically holds the clip 20 in its open configuration. Suture 56 extends from the suture clip 20, with suture leads 56a and 56b extending through the clip inner lumen 48 via the clip distal opening 50, engagement tab 54, and proximal opening 52. By virtue of the vacuum, the suture leads 56a, 56b pass through device inner member distal opening 30 and inner member lumen 32, exiting the inner member 26 of the device via suture recess 82, and exiting the side of main body 12 (not shown). The user is then able to manually adjust the tension in the suture prior to securing the suture in place.

Clip deployment occurs when the device 10 is mechanically actuated by the user via the mechanical advancer button 84. In one embodiment, the button 84 is depressed causing the inner body 26 to be at least partially retracted within the device 10. During actuation, as shown in FIGS. 2A-B, the inner body 26 begins to move proximally toward the distal end 16 of the device 10. With this action, the length of the inner body 28 outside of the device 10 is decreased and the proximal end of the most proximal clip 20 abuts the distal end 16 of the device 10 forcing the most distal clip 20 to edge off of the distal end 28 of the inner body 26. Once the clip 20 is completely off of the inner body 28 and strung onto suture 56, the clip assumes its "closed position" as described above with reference to FIG. 4 and locks the suture in place. The user then withdraws the suture clip device 10 from the patient, leaving the suture 56 and suture clip 20 in place in the desired tissue.

The device inner body distal end 28 retracts into the main body distal opening 24 by manipulation of the mechanical advancer button 84. With the inner body distal end 28 retracted, the suture clip 20 is released from the device 10, as shown in FIG. 5B. As the inner body distal end 28 is retracted, the suture clip 20 is engaged against the distal edge 25 of the main body distal opening 24 and is forced off of the inner body distal end 28 at a position adjacent the material portions 58a, 58b. With the suture clip 20 freed from the device, the clip 20 assumes its closed (i.e., bent) configuration, with the clip body 44 bent and the engagement tabs 54a, 54b projecting inward to at least partially obstruct or even to completely close the clip inner lumen 48 while engaging the suture lines 56a, 56b. With the suture clip 20 in this closed configuration, the suture lines 56a, 56b are held fast and cannot move longitudinally within the suture clip 20. The suture lines 56a, 56b are thus held by the combination of tab to inner wall interaction/forces and by the tortuous path that the tabs 54a, 54b and bent clip body 44 force the suture lines 56a, 56b to follow, which provides more surface area contact with the suture lines 56a, 56b to increase retention. Note that the suture lines 56a, 56b still pass into the device 10, exiting the inner body 26 via suture recess 82 and exiting the side of main body 12 through suture recess 82. FIG. 5C depicts the device inner body 26 retracted even further within the device main body 12.

Figure 6A:
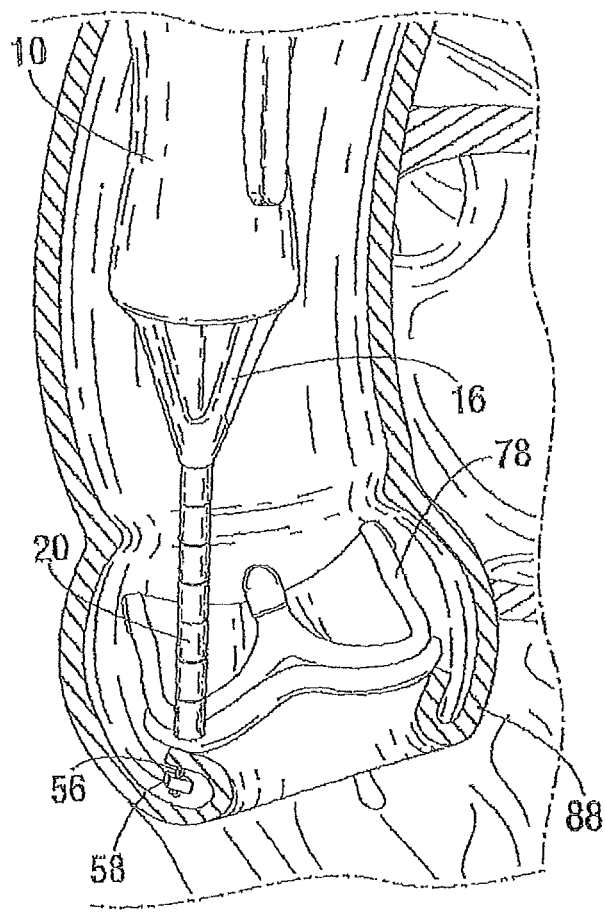
FIGS. 6A and 6B illustrate the device of FIG. 1 advanced within a patient's body and being utilized to secure an artificial heart valve to existing heart tissue according to an embodiment of the invention.
Figure 6B:
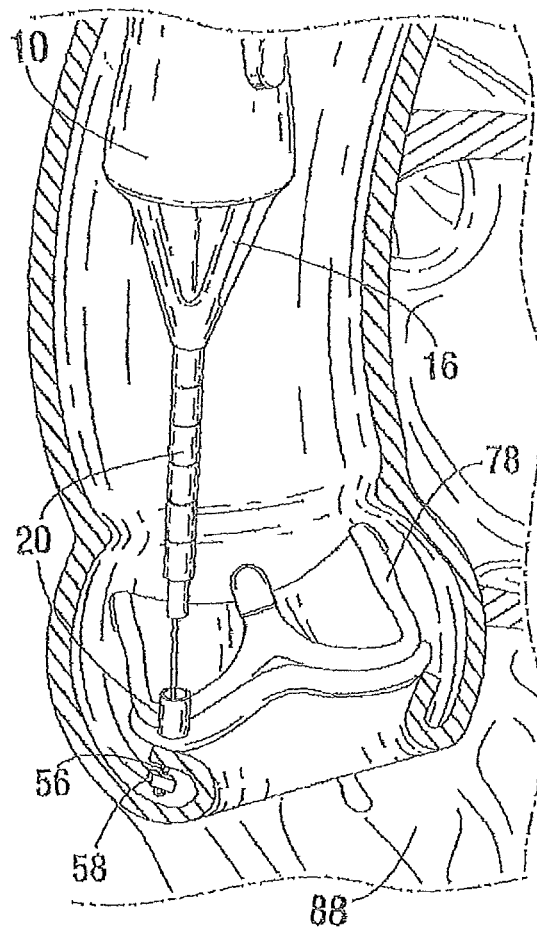
Figure 8D:
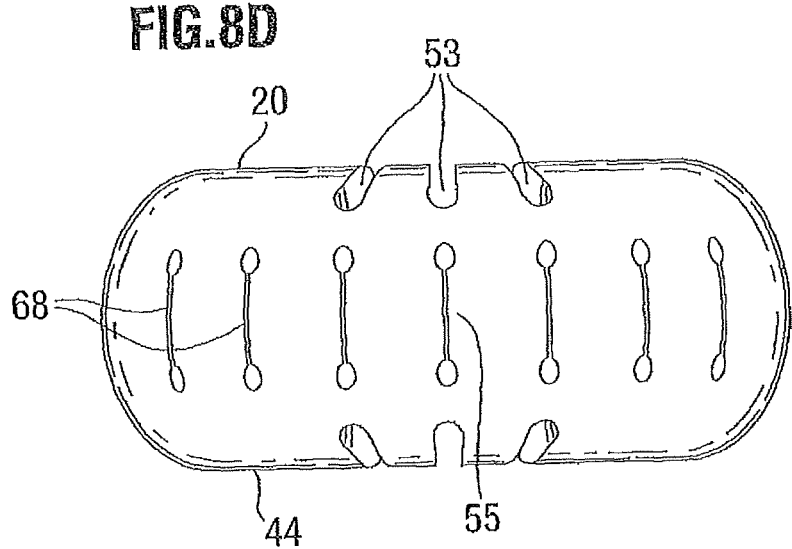
Figure 8E:
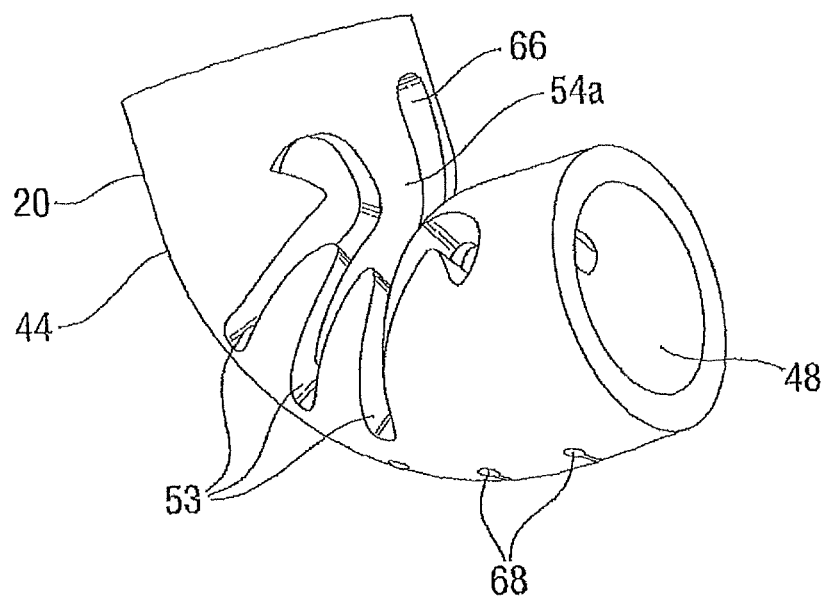

FIGS. 6A and 6B illustrate a particular use for the device 10 to secure with a clip sutures used to attach two layers together, wherein one layer is a cardiac implant 78, such as an artificial valve implant and the other is a heart valve annulus. In the embodiment depicted, the suture 56 has previously been passed through the desired material structures within the patient's body. After suturing the implant 78 to the heart tissue 88 with suture 56, the user approaches the suture lines with the distal end 28 of the inner body 26 of the device 10. Vacuum is applied to the device; in some cases, the user covers the suture recess 82 with his finger to enable suction throughout the length of the device. With the vacuum source connected to the vacuum port 80, negative pressure is created within the inner body 26 of the device along its length from the vacuum port 80 to the distal end 28. The suture lines 56 are drawn into the distal end 28 of the inner body 26 and through the device 10, exiting the device 10 at the suture recess 82. The user can then adjust the tension in the suture 56 using the portions of the suture that are outside the device 10. The user can verify the effectiveness of the tightened suture 56 by monitoring various patient functions. For example, the user may confirm the result by monitoring blood flow using radiopaque dyes combined with fluoroscopy. If the user is dissatisfied with the results when the suture 56 is initially tightened, the user can remove the suture 56 entirely from the patient's body and repeat the suture deployment to try to achieve a better positioning of suture. If, however, the user is satisfied with the results, the user deploys the suture clip 20 from the device 10.

Referring still to FIGS. 6A and 6B, after placement of the suture at the desired location and achieving the desired tension, the suture clip 20 is deployed from the delivery device 10. The suture clip 20 is released from the distal end of the device 10, securely holding the suture 56 in place. The user can then cut the free end(s) of the suture 56 and remove any excess suture by simply pulling the excess suture out of the patient's body. The user then withdraws the suture clip device 10 from the patient, leaving the suture 56 and suture clip 20 in place.

Note that the number, shape, and configuration of the engagement tabs and hinge points on a particular clip can vary, depending on the particular application. For example, the engagement tabs can be positioned on opposing sides of the clip, on the same side of the clip, in a spiral pattern about the clip body, etc. Similarly, the hinge points can be positioned on opposing sides of the clip, on the same side of the clip, in a spiral pattern, etc.

Various methods and/or systems can be used to pass the suture through the desired material, as is well known in the art. Moreover, although FIGS. 6A and 6B depict the device used to replace a heart valve, the device can also be used in other procedures, including material treatments such as so-called "edge-to-edge" mitral valve repairs involving edge-to-edge suturing of adjacent mitral valve leaflets. Embodiments of the system may be used to occlude a left atrial appendage for decreasing the risk of arterial embolism, for example. In another procedure, material along the ostium of the left atrial appendage is sutured together to prevent blood from flowing in and out. This procedure is preferably performed using a transeptal approach and may be performed after delivering an expandable device into the left atrial appendage for filling the volume and further preventing the formation of thrombus. In another method of use, the system may be used for occluding fallopian tubes in a minimally-invasive sterilization technique. In this procedure, the system is advanced into a fallopian tube and suture is applied to pull opposing walls together, thereby blocking the tube. In still other applications, the system may be used to treat organ prolapse, such as uterine or bladder prolapse. This procedure may be used to pull tissue together in a percutaneous procedure to treat prolapse by providing additional support at locations wherein muscles and/or ligaments have become stretched or have been otherwise damaged.

Additional information on procedures for which the surgical clip delivery device can be useful are disclosed in the following references, the entire contents of which are expressly incorporated herein by reference: U.S. Pat. No. 6,626,930 issued to Allen et al.; U.S. patent application Ser. No. 10/106,583, filed Mar. 26, 2002 and entitled, "Sequential Heart Valve Leaflet Repair Device and Method of Use"; U.S. patent application Ser. No. 10/233,879, filed Sep. 3, 2002 and entitled "Single Catheter Mitral Valve Repair Device and Method"; U.S. patent application Ser. No. 10/389,721, filed Mar. 14, 2003 and entitled "Mitral Valve Repair System and Method of Use"; and U.S. patent application Ser. No. 11/174,143, filed Jun. 30, 2005 and entitled "System, Apparatus, and Method for Repairing Septal Defects."

FIGS. 7A-7F and 8A-8E depict, in open and closed configurations, respectively, additional clip configurations. The suture clip 20 is initially formed from a generally tubular body 44, such as a portion of nitinol hypotube into which the desired pattern of tabs 54a, 54b, tab stress cutout windows 66, bending notches 53, and stress-relief cuts 68, etc., is formed.

Note that the clip 20 including the pattern of tabs 54a, 54b, etc., can be formed in various ways, depending on the particular application. For example, injection molding, die and coining, laser cutting, machining, and shape setting can be used, alone or in combination, depending on the particular clip configuration and materials. In one embodiment, the pattern is formed by laser cutting the desired pattern into a portion of a hypotube or other generally tubular body. FIGS. 7A-7F depict the generally tubular body 44 after the desired pattern has been cut into the generally tubular body, but before the tubular body has been bent and before the tabs 54a, 54b have been bent or otherwise moved and set into position to block the inner lumen 48. The configuration depicted in FIGS. 7A-7F also corresponds with the "open" configuration of the clip 20.

FIGS. 8A-8E depict the clip 20 of FIGS. 7A-7F, but with the clip body 44 bent and the tabs 54a, 54b bent into and set in their "closed" position, wherein the inner lumen 48 is at least partially blocked. The notches 53 on either side of the clip 20 create a hinge point 55 about which the clip 20 can easily bend. (Note that, although the term "hinge point" is used herein, the actual bending may occur over a relatively large area, as is shown in the embodiment of FIGS. 8A-8E.) The tab stress cutout windows 66 enhance the flexibility while maintaining strength of the tabs 54a, 54b, and also reduce stress on the hinge-like portion where each tab 54a, 54b connects to the generally tubular body 44 of the clip 20. The stress relief lines 68, which are on the same side of the clip 20 as the hinge point 55, help to relieve stress that might build up on that side of the clip body 44 as the clip 20 assumes its bent configuration. In the embodiment of FIGS. 8A-8E, the free ends of the engagement tabs 54a, 54b are directed toward each other, and are both on an opposite side of the clip body 44 from the hinge point 55.

Figure 9:
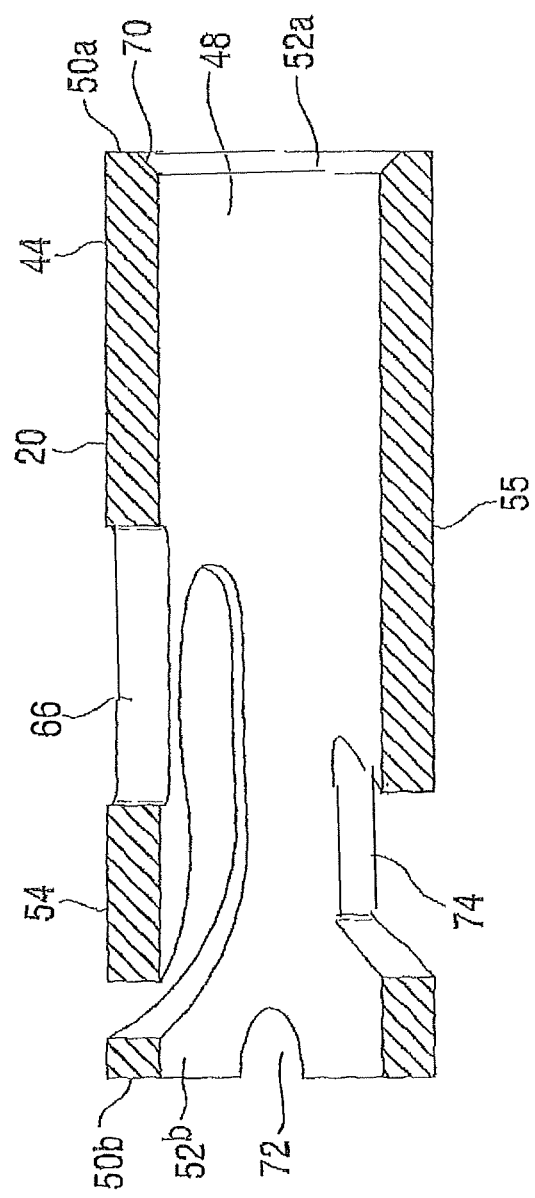
FIG. 9 depicts a side view, in cross section, of a suture clip according to an embodiment of the invention.

FIG. 9 depicts, in cross section, a side view of a further embodiment of a clip 20. The clip 20 includes a single tab 54 positioned across from a hinge point 55. The clip 20 includes a beveled inner edge 70 at one or more of the clip openings, such as the clip distal opening 50 as depicted. The beveled inner edge 70, which in the embodiment depicted is at an angle of about 45 degrees, can assist in threading suture into the clip 20 through the clip distal opening 50. The clip 20 can also include one or more generally semi-circular openings 72 at one or more openings such as the clip proximal opening 52. The semi-circular openings 72 can aid in processing of the clip during manufacture, e.g., permitting easy alignment and holding of the clip 20 during bending and/or shape setting of the clip body 44 and tabs 54a, 54b, etc. After clip manufacturing is complete, the semi-circular openings 72 can interact with corresponding structure on the device distal end to assist in alignment and positioning of the clip 20 on the device distal end.

The clip 20 depicted in FIG. 9 also includes a window-like opening 74 aligned opposite to the free edge of the tab 54, positioned so that when the tab 54 extends into the inner lumen 48 the free edge of the tab 54 can rest within the window-like opening 74, but without extending out of the clip 20 itself. The window-like opening 74 permits tab 54 to be bent or otherwise positioned so that the tab free edge extends across and just beyond the inner lumen 48, thereby compensating for any backward tab movement (either through material recovery or outward pressure from the suture lines, etc.) that might occur after the tab 20 is initially deployed to its closed configuration. Note that a window-like opening such as element 74 from FIG. 9 could be positioned at or near a hinge point, so that the window-like opening serves multiple purposes: receiving the tab free edge, relieving stress that might develop adjacent the hinge point, and providing for relatively easy bending or flexing of the clip body about the hinge point.

Figure 10:
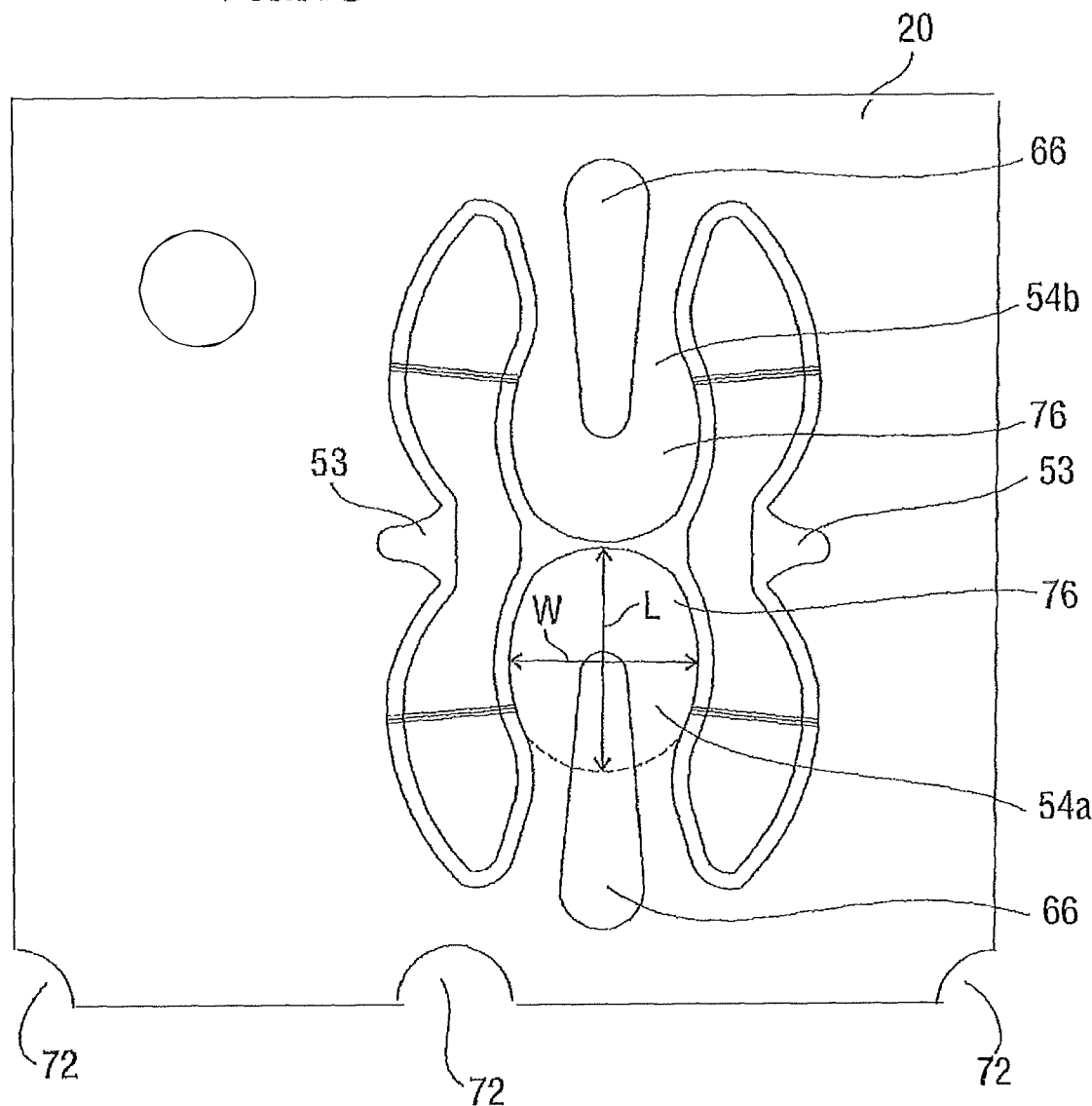
FIG. 10 depicts a plan view of a cut-out pattern for a suture clip according to an embodiment of the invention.

FIG. 10 depicts a cutout pattern (in flattened or unrolled configuration) for creating the suture clips. The generally elliptically-shaped portion 76 of each the tabs 54a, 54b (with 54b having a dashed portion depicting an imaginary completion of the "ellipse" that forms the actual tab) has a width W (i.e., minor axis) that is approximately equal to (but still slightly less than) the diameter of the clip inner lumen 48. The generally elliptical shaped portion 76 has a length L (i.e., major axis) that is greater than the diameter of the clip inner lumen 48. These dimensions permit each tab 54a, 54b, when in the closed configuration, to fit within the clip inner lumen 48 and still close off essentially the entire diameter of the clip inner lumen 48, thereby securely holding any suture passing therethrough.

Note that because the pattern of tabs and windows may have been cut in a radial manner into the generally tubular body 44 of the clip 20, the tabs 54a, 54b each have an inner surface having an "inner" elliptically-shaped portion that is somewhat smaller in width than its corresponding "outer" elliptically-shaped portion 76 discussed above. Accordingly, the relatively narrow width of each tab's respective inner elliptically-shaped portion may only partially obstruct the inner lumen 48. However, the tab outer surface has the full width W of the elliptically-shaped portion 76 shown in FIG. 10, and it is this width (W) of the "outer" elliptically-shaped portion 76 that obstructs the remaining diameter of the inner lumen 48 when a tab 54a, 54b extends into the inner lumen 48.

The dimensions of the clip can vary depending on the particular application. In one embodiment, a clip 20 such as that depicted in FIGS. 7A-7F has a length of about 0.13 inches, an inner lumen diameter of about 0.030 inches, and an outer diameter of about 0.046 inches. A clip of this size can receive and secure multiple suture lines having various diameters, including sutures having diameters ranging from 0.006 to 0.008 inches. Other clip dimensions are also within the scope of the invention, with the clip dimensions varying depending on aspects of the particular application, e.g., suture type and diameter, the type of material to be repaired, the number of suture lines being secured by the clip, etc. Additionally, although the particular embodiments depicted have used the clip to secure two suture lines, the clip could be used to secure a single suture line or multiple suture lines. For multiple suture lines, two or more of the multiple suture lines could be portions of a common suture line. For example, a clip could be used to secure four suture lines, with two of those suture lines being opposing portions of a first common suture line and the other two suture lines being opposing portions of a second common suture line. Note that the embodiments depicted are only a few examples of many that are within the scope of the invention. Depending on the particular embodiment, the tab and other cut-outs could be formed in various shapes, and they could be aligned in a common direction with other cutouts, be in opposite directions of alignment, and/or could be positioned in various directions along the clip outer wall.

Figure 11A:
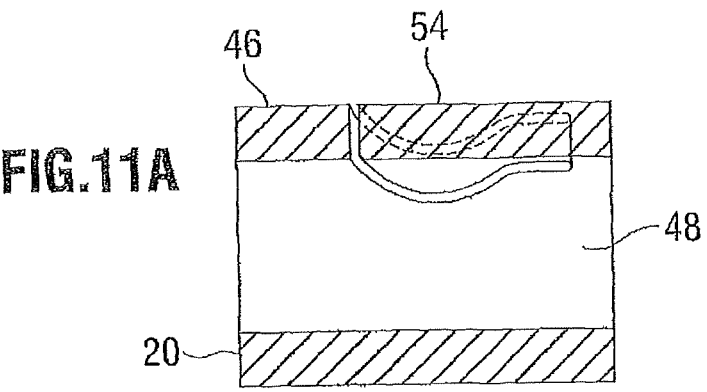
FIG. 11A-11C depict side views, in cross-section, of suture clips according to various embodiments of the invention.
Figure 11B:
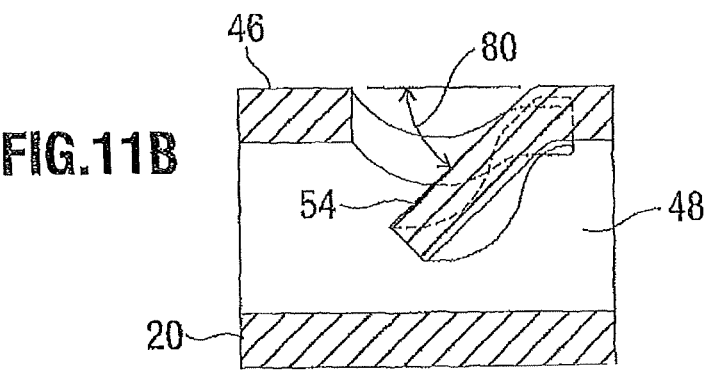
Figure 11C:
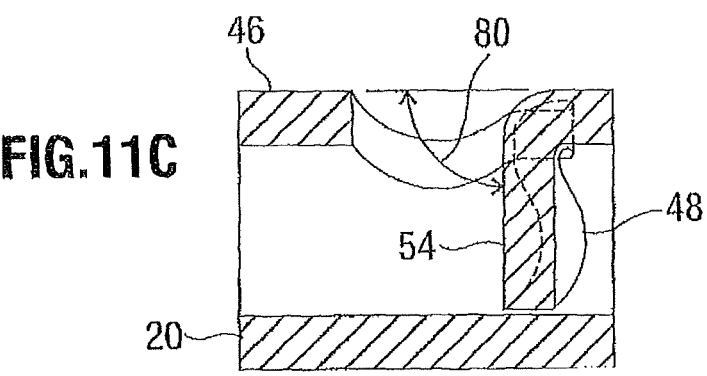

FIGS. 11A-11C depict in cross-section an engagement tab 54 in various configurations. In the embodiment of FIG. 11A, the engagement tab 54 is generally aligned with the clip outer wall 46, so that the clip inner lumen 48 is generally unobstructed. In FIG. 11B the engagement tab 54 is positioned to extend partially into the lumen 48, with the angle 80 between the engagement tab 54 and adjacent portion of the clip outer wall 46 being on the order of 45 degrees. FIG. 11C depicts the engagement tab 54 extending to a maximum extent into the clip lumen 48, with the angle 80 between the engagement tab 54 and adjacent portion of the clip outer wall 46 being on the order of 90 degrees. Note that various angles 80 are within the scope of the invention, depending on the particular embodiment and such factors as the size of the suture, the size of the clip, the percentage of the inner lumen that is desired to be obstructed, the length of the engagement tab with respect to the inner diameter of the lumen, the bend added to the clip body 44, etc.

Figure 12A:
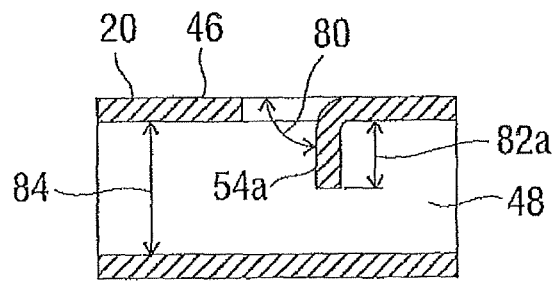
FIGS. 12A-12C depict side views, in cross-section, of suture clips according to various embodiments of the invention.
Figure 12B:
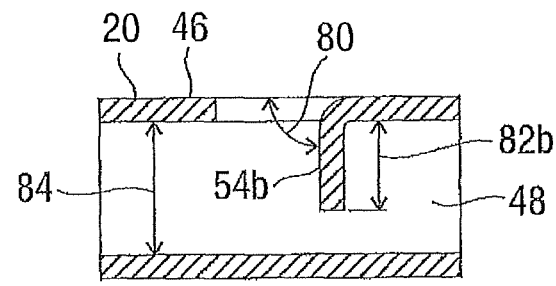
Figure 12C:
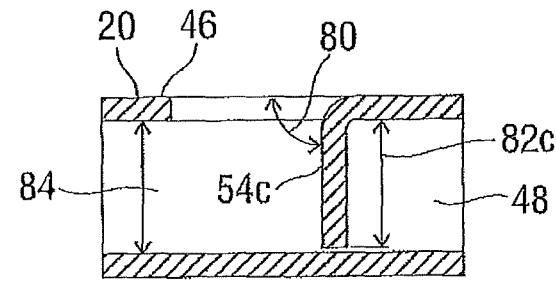

FIGS. 12A-12C depict clips 20 having various lengths 82 of engagement tabs 54. Although the embodiments of FIGS. 12A-12C are all depicted as having an angle 80 of about 90 degrees, it is noted that other angles are within the scope of the invention, as discussed above with respect to FIGS. 11A-11C. In FIG. 12A, the engagement tab 54A has a length 82A equal to about 50% of the clip inner lumen diameter 84. In FIG. 12B, the engagement tab 54b has a length 82b of about 75% of the clip inner lumen diameter 84, while in FIG. 12C the engagement tab 54c has a length 82c of about 100% of the clip inner lumen diameter 84. Note that, as with the angle 80, the engagement tab length 82 for a particular clip can vary depending on the particular application and still fall within the scope of the invention.

Figure 13A:
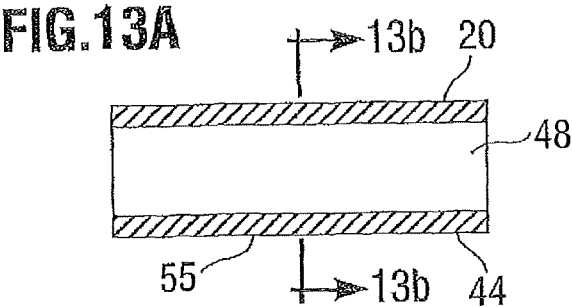
FIGS. 13A and 13B depict cross-sectional side and end views, respectively, of a suture clip in an open configuration according to an embodiment of the invention.
Figure 13B:
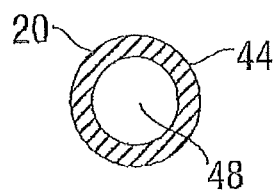
Figure 14A:
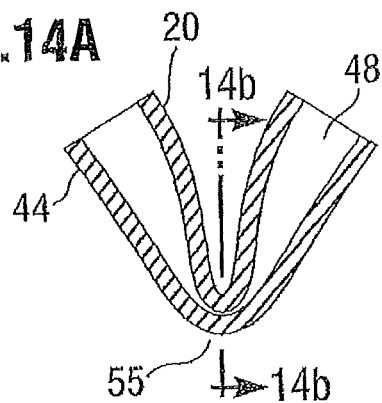
FIGS. 14A and 14B depict cross-sectional side and end views, respectively, of the suture clip of FIGS. 13A and 13B in a bent (closed) configuration.
Figure 14B:
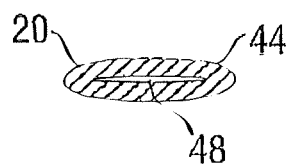

Note that the bending of the clip body 44 itself can effectively block a clip inner lumen, with or without engagement tabs such as those (54, 54b, 54c) depicted in FIGS. 12A-12C, etc. FIGS. 13A-13B and 14A-14B depict a clip 20 having a hinge point 55, but without tabs or other projections inside the inner lumen 48. In FIGS. 13A-13B, the clip body 44 is in its straight or open configuration, without any bending about the hinge point 55. The inner lumen 48 is seen in FIG. 13B as being essentially open and unobstructed adjacent the hinge point 55. In FIGS. 14A-14B, the clip 20 is in its bent or closed configuration, with a relatively sharp bend in the clip body 44 adjacent the hinge point 55. The inner lumen 48 is seen in FIG. 14B as being almost entirely blocked adjacent the hinge point 55. Note that although a single hinge point 55 and associated bend is depicted in FIGS. 14A-14B, a suture clip according to the invention could include multiple hinge points and associated bends along the length of the suture clip.

Figure 15A:
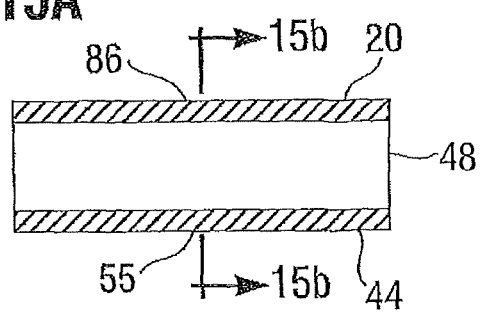
FIGS. 15A and 15B depict cross-sectional side and end views, respectively, of a suture clip in an open configuration according to an embodiment of the invention.
Figure 15B:
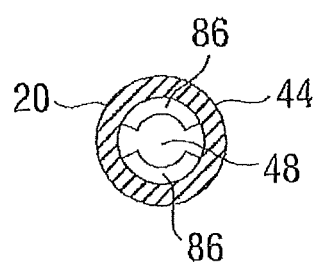
Figure 16A:
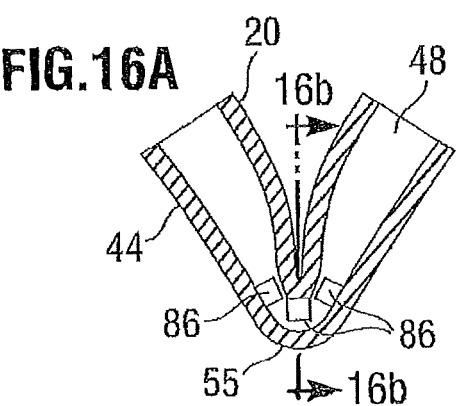
FIGS. 16A and 16B depict cross-sectional side and end views, respectively, of the suture clip of FIGS. 15A and 15B in a bent (closed) configuration.
Figure 16B:
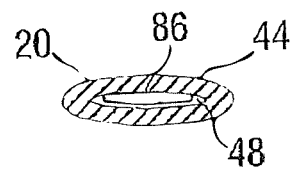

FIGS. 15A-15B and 16A-16B depict a clip having a hinge point 55 with inward-facing obstructions in the form of inner bumps 86 that extend into the clip inner lumen 48 at or adjacent the hinge point 55. In FIGS. 15A-15B, the clip 20 is in the open configuration, with the inner lumen 48 being generally unobstructed adjacent the hinge point 55 except for minimal areas covered by the inner bumps 84, as depicted in FIG. 15B, so that the inner lumen 48 has a size sufficient for suture to slidingly pass therethrough. FIGS. 16A-16B depict the same clip 20 in its closed configuration, wherein the clip body 44 is bent and has an almost flattened shape adjacent the hinge point 55, as depicted in FIG. 16B. With the bumps 86 engaging against each other and/or the clip wall, the inner lumen 48 is generally obstructed adjacent the hinge point 55 so that suture lying within the inner lumen 48 will be held fast.

Clips can be formed from various biocompatible materials, including shape memory and/or pseudoplastic materials such as nitinol. In one embodiment a suture clip is formed from nitinol (such as an alloy of nickel at 54.5-57% by weight with titanium accounting for the balance except for residual amounts (less than 0.05% each) of oxygen, carbon, and hydrogen) or another shape memory and/or pseudoplastic material, with the suture clip formed so that the clip assumes its closed position (i.e., with the clip body in the bent configuration and the clip engagement tabs extending into the clip inner lumen) when in the austenite condition (i.e., when generally unstressed at body temperature). The nitinol can have an austenite finish temperature selected to match the particular application. In a medical suture clip, an austenite finish temperature of −5 degrees to +15 degrees Celsius may be selected.

A suture clip can be formed from material that will assume its martensite condition when subjected to sufficient stress, such as the stress applied to the clip engagement tabs 54 and clip body 44 when the suture clip 20 is mounted onto the device inner body distal end 28, as depicted in FIG. 5A. In such an embodiment, the device inner body distal end 28 applies stress to the clip body 44 and clip engagement tabs 54, forcing the clip body 44 to be straight and the clip engagement tabs 54 into general alignment with the clip outer wall 46. The stressed material, including the bent material where the clip engagement tabs 54 meet the rest of the clip outer wall 46, is forced into its martensite condition. Then the stress is removed, such as where the suture clip 20 is removed from the device 10 and device inner body distal end 28 as depicted in FIGS. 5B and 5C, the material returns to its austenite condition so that the clip body 44 assumes its bent shape and the clip engagement tabs 54 are biased inwardly to at least partially block the clip inner lumen 48.

FIGS. 17-25 illustrate an exemplary suture clip deployment device 100. The device 100 can be loaded with one or more suture clips and can be used to deploy the suture clips onto sutures, such as during implantation of prosthetic device within the heart. The device 100 comprises a handle portion 102 that can be held and actuated by a user and a shaft portion 104 that can be inserted into the body, at least partially, to deploy suture clips onto sutures in hard to reach regions within the body in a minimally invasive manner. The device 100 can be used with any of the suture clips described herein or their equivalents, which are collectively referred to with the reference number 130 below. FIG. 17A shows the device 100 with exemplary sutures 131 inserted into the distal end of the device. FIG. 17B shows the shaft portion 104 of the device 100 with a suture 131 passing through an inner lumen of the device 100 with a free end of the suture projecting out through a lateral opening in the device, as describe in more detail below.

The handle portion 102 includes one or more actuation mechanisms that control functions of the device 100. For example, the trigger 106 and associated mechanisms within the handle portion 102 can control a vacuum system either in the device 100 or remotely coupled to the device, and the lever 108 and associated mechanisms within the handle portion can control suture clip deployment, suture cutting, and/or advancement of remaining suture clips loaded on the device 100.

As shown in FIGS. 18A-18F, the shaft portion 104 can comprise a main shaft or hypotube 120, a vacuum tube 122, a clip plow or pusher 126, one or more clips 130, an outer tube 132, a clip guide 138, a knife tube 140, a suture door 152, and/or other components. The shaft portion 104 is also shown assembled in FIGS. 23A-23F.

Figure 17A:
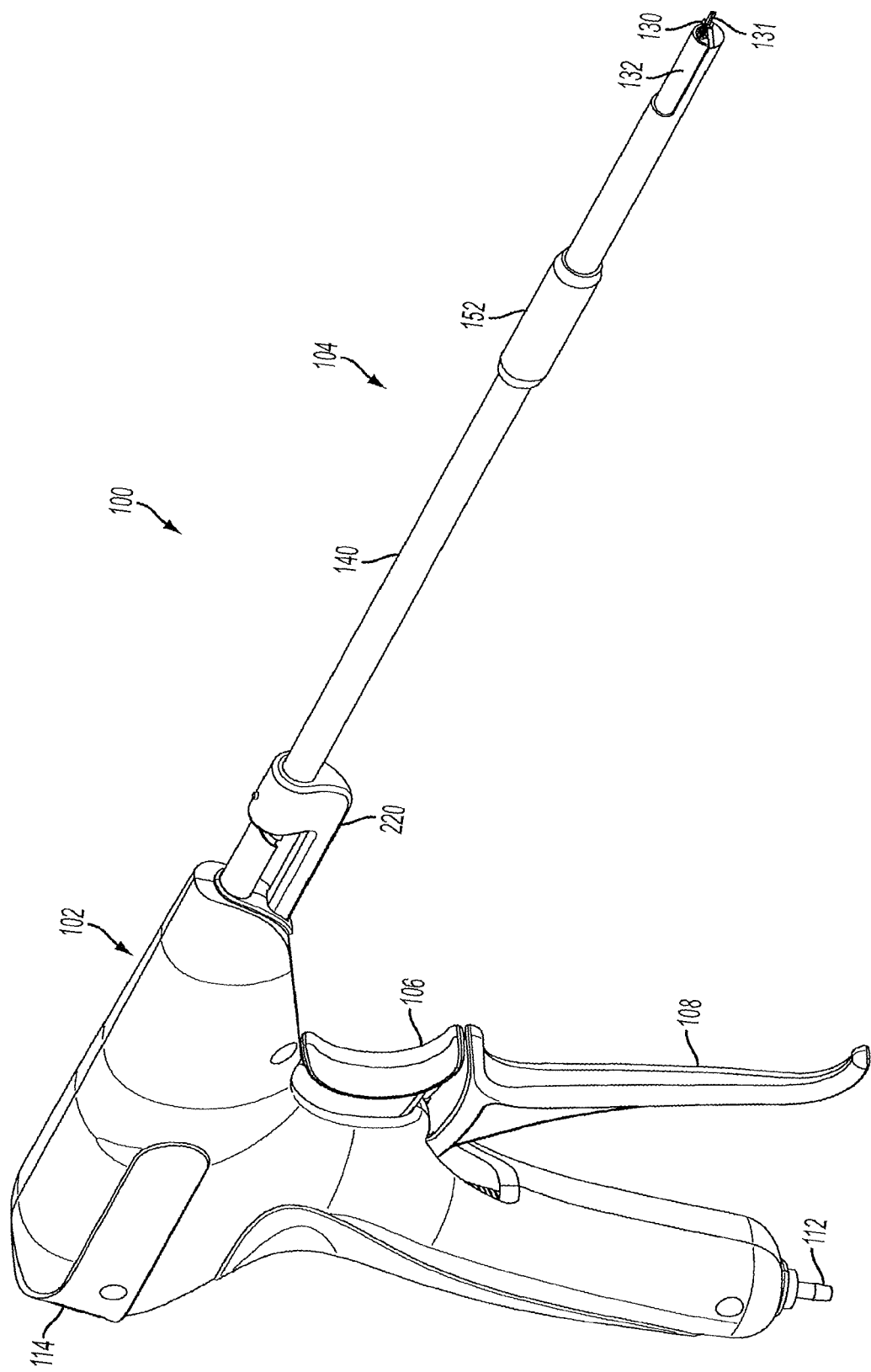
FIG. 17A is a perspective view of another exemplary suture clip deployment device.
Figure 17B:
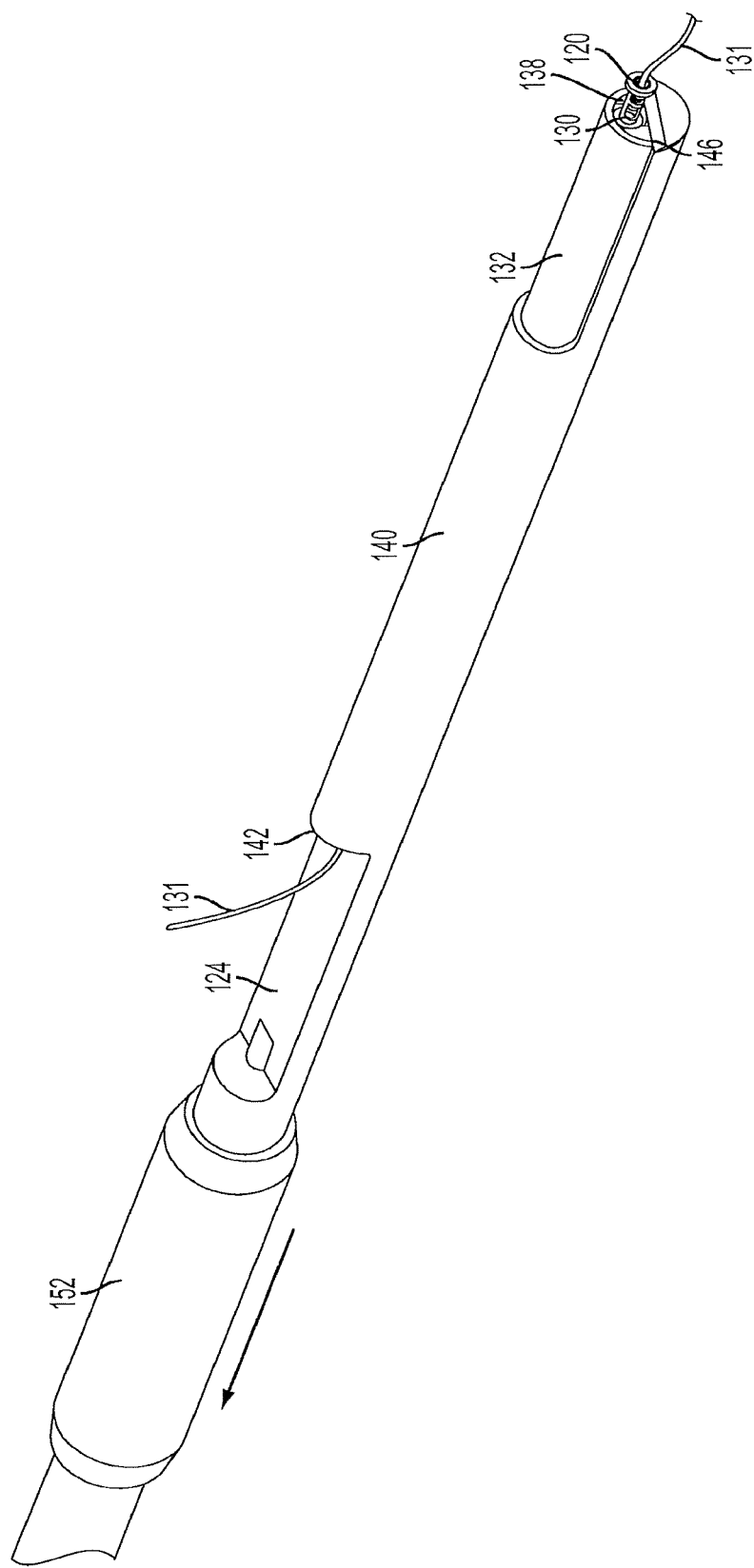
FIG. 17B is a perspective view of a shaft portion of the device of FIG. 17A.
Figure 18A:
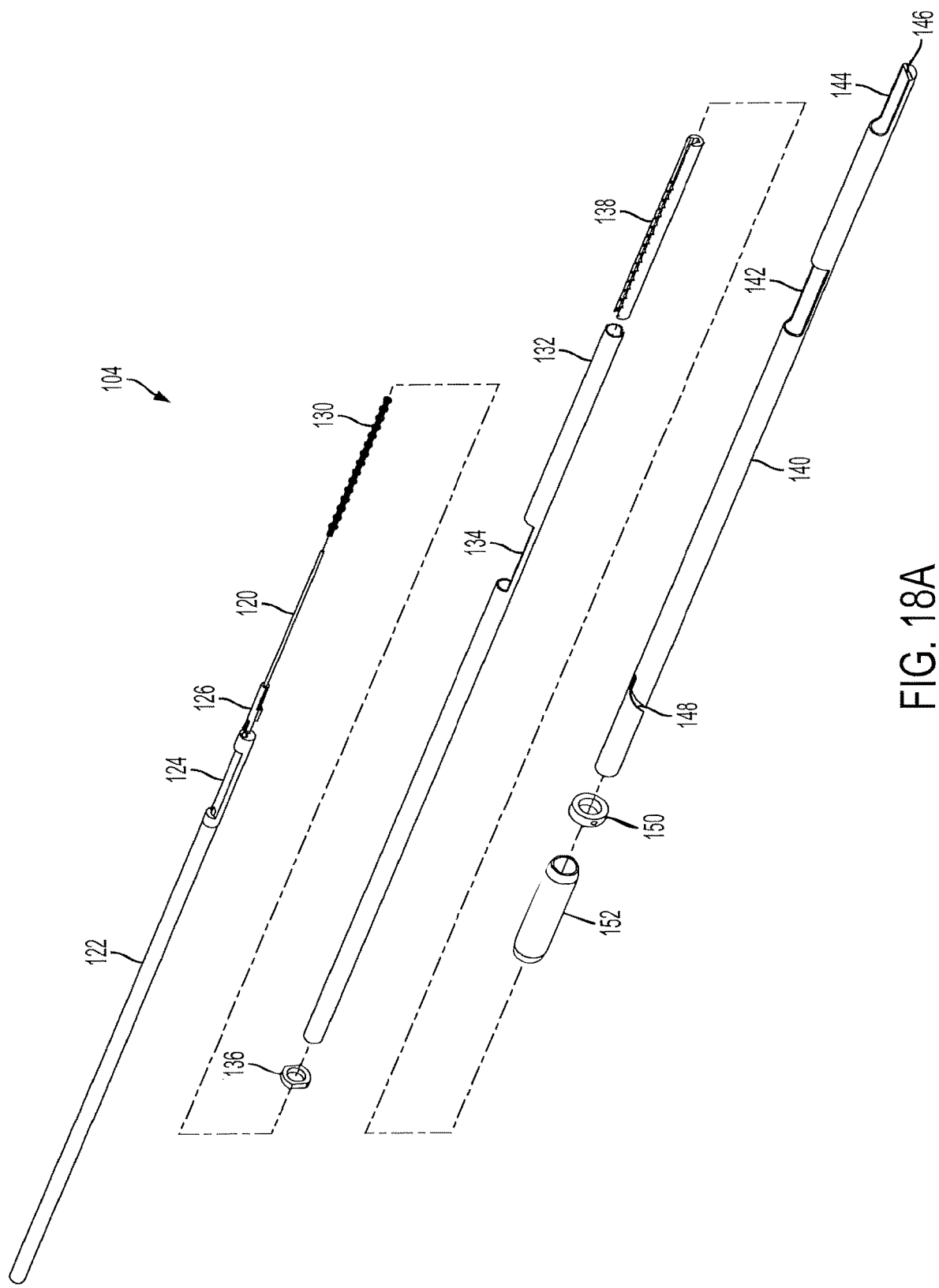
FIG. 18A is an exploded view of the shaft portion of the device of FIG. 17A.
Figure 18B:
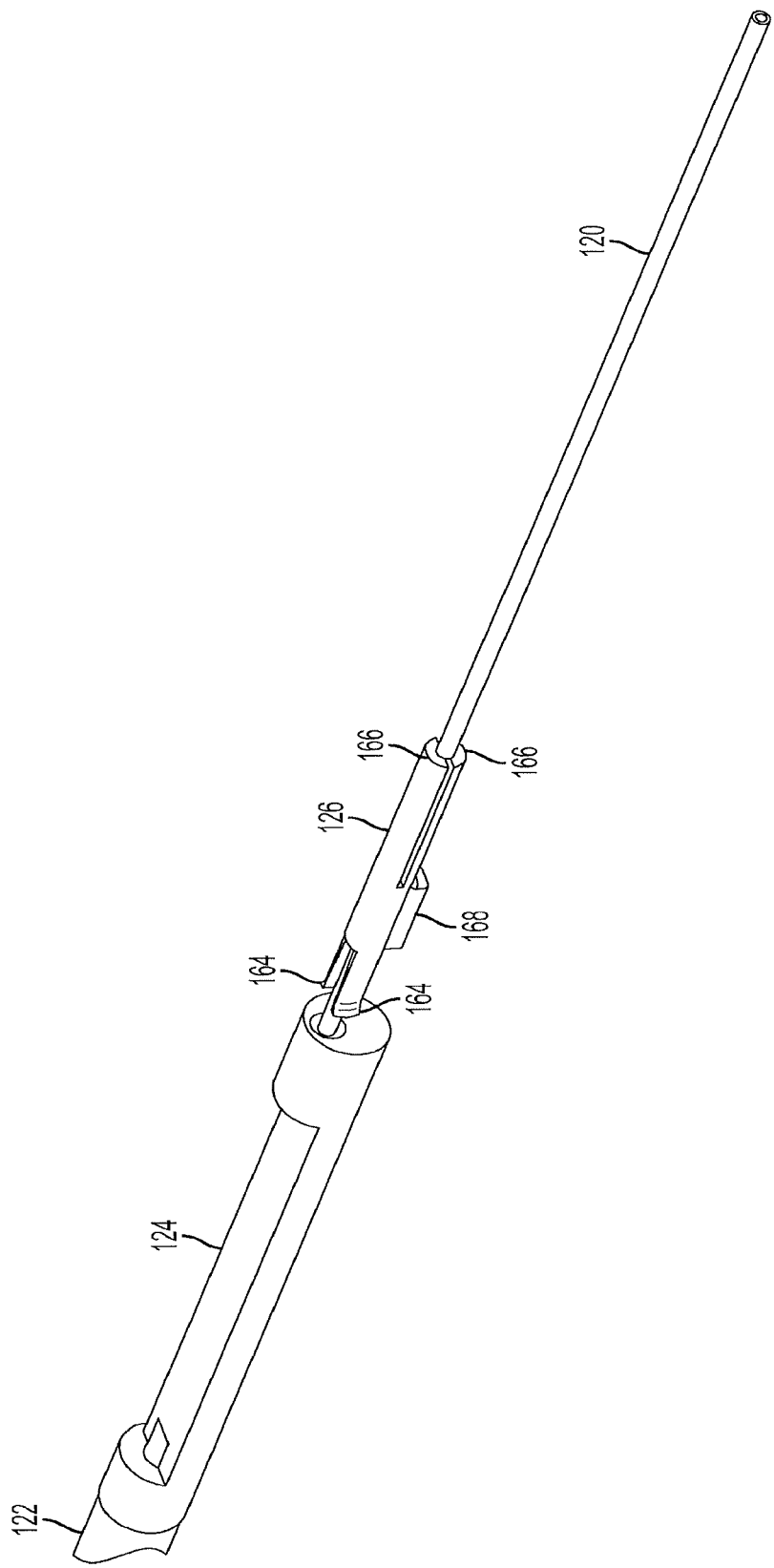
Figure 18C:
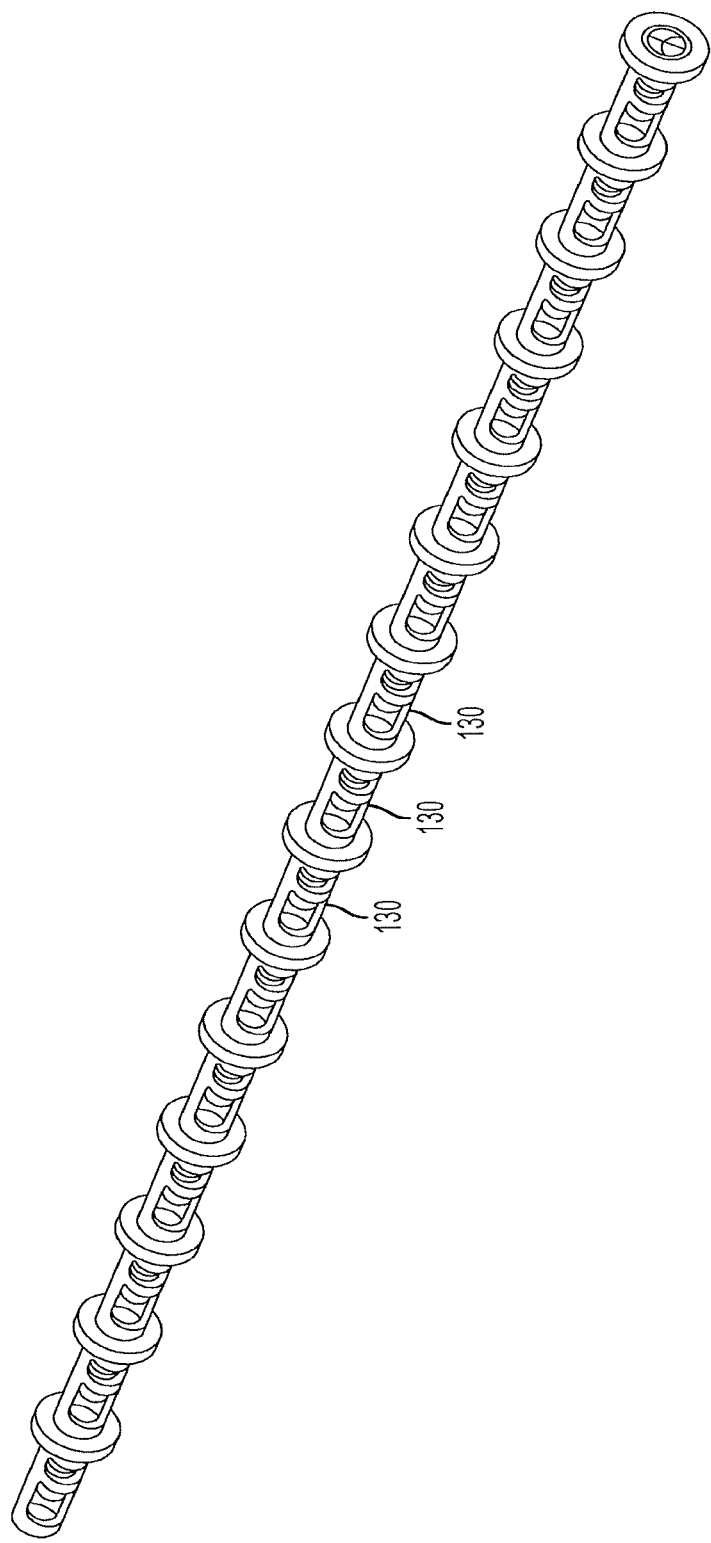
Figure 18D:
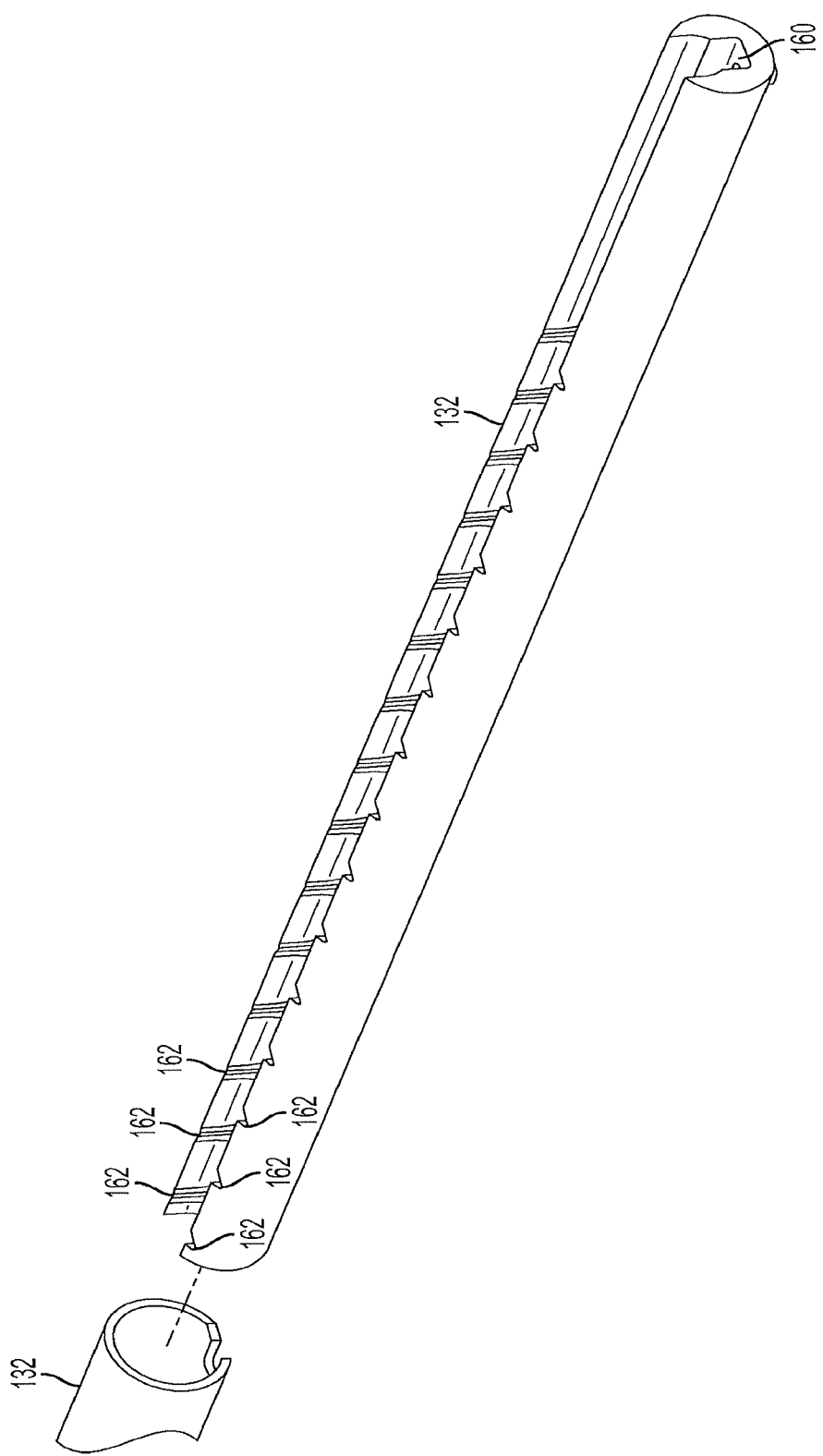
Figure 23D:
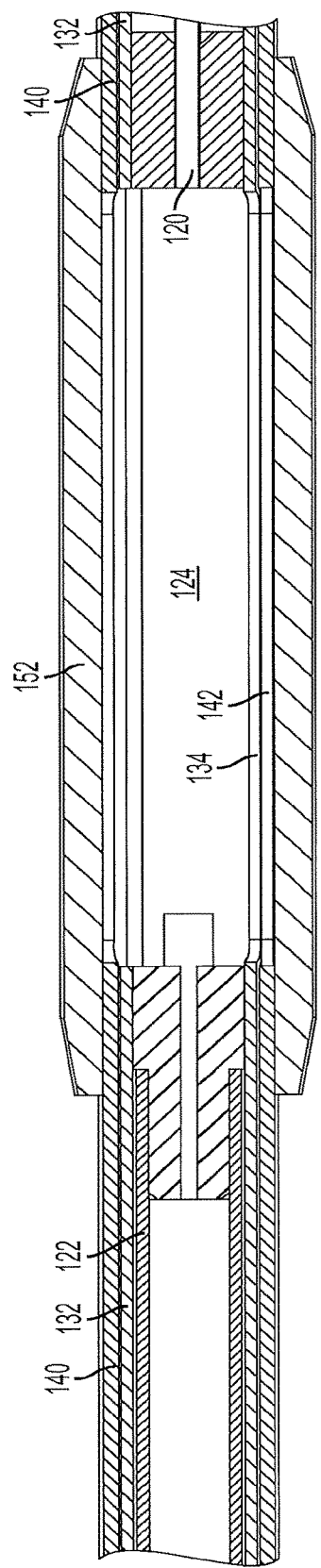

The hypotube 120 can be a tubular shaft having an inner lumen with distal opening, as shown in FIG. 18B. The clips 130 are mounted in axial alignment on the outer surface of a distal end portion of hypotube 120, as shown in FIG. 18C. The device can be configured to be loaded with any number of clips 130, such as up to 10 or 15 clips. As shown in FIG. 18B, the vacuum tube 122 can comprise a vacuum chamber 124 at a distal end. The vacuum chamber 124 is partially open on an upper side to expose a lumen within the vacuum tube 122. A cross-sectional view of the vacuum chamber 124 and adjacent components is shown in FIGS. 23C and 23D. A distal end of the vacuum chamber 124 is attached to a proximal end of the hypotube 120 such that an inner lumen of the hypotube is in fluid communication with the inner lumen of the vacuum chamber 122 and the open portion at the vacuum chamber 124. The suture door 152 can cover the vacuum chamber 124 to close off the opening and the inner lumen when a vacuum is applied to the inner lumen, as described below. When the suture door 152 is open, one or more sutures 131 drawn through the inner lumen from the distal opening of the hypotube 120 can be drawn out laterally from the inner lumen through the opening in the vacuum chamber 124, as shown in FIG. 17B.

Figure 23E:
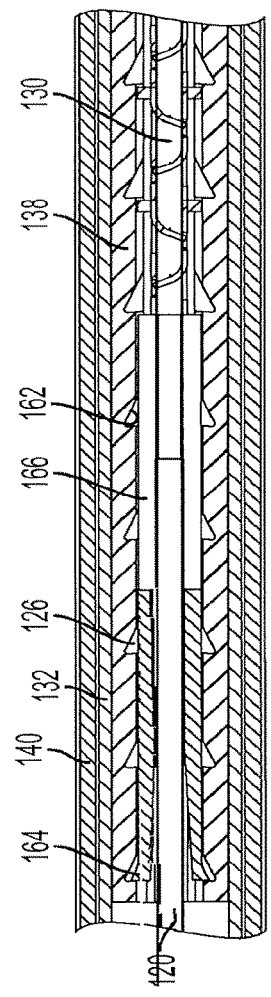
Figure 23F:
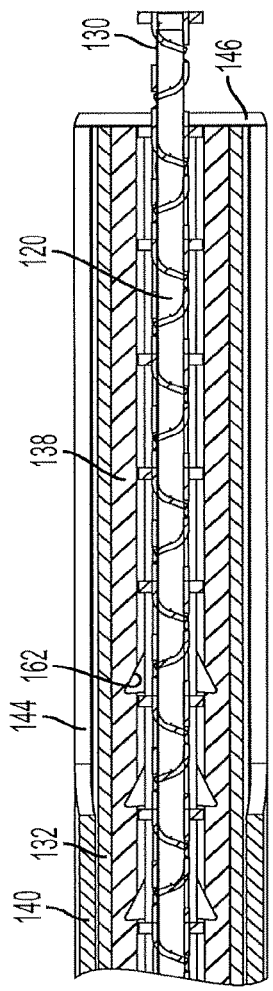

The clip plow 126 is positioned around the hypotube 120 and configured to drive the clips 130 distally along the hypotube 120, as shown in FIG. 23E. The hypotube 120 passes between two split distal portions 166 of the clip plow, as shown in FIG. 18B, which are frictionally engaged with the outer surface of the hypotube 120. This frictional engagement causes the clip plow 126 to tend to move axially along with movement of the hypotube 120 via the actuation mechanisms in the handle portion 102 unless the frictional engagement between the clip plow and the hypotube is overcome by another axial force on the clip plow.

The clip plow 126 is positioned within the clip guide 138, as shown in FIGS. 18B and 23E. The clip guide 138 comprises a channel 160 in which the plow 126, the hypotube 120 and the clips 130 travel axially. The channel 160 can include a keyed geometry that corresponds to the shape of a key portion 168 of the plow (see FIG. 18B) to maintain rotational orientation. The channel 160 further comprises a plurality of grooves 162 on either side of the channel that are spaced apart axially about the length of one clips 130. The grooves 162 engage with prongs 164 at the proximal end of the plow 126 to create a ratcheting mechanism that allows the plow 126 to move distally relative to the guide 138 but not proximally. When the hypotube 120 and vacuum tube 122 are moved distally by the actuation mechanism in the handle portion, the frictional engagement between the plow 126 and the hypotube 120 pulls the plow 126 distally. Because the prongs 164 have a sloped distal surface, the prongs 164 can flex inwardly and exit the grooves 162 of the guide 132 in response to the distal friction force exerted on the plow 126 by the hypotube 120. When the prongs 164 disengage from the grooves 162, the plow 126 can be pulled distally along the guide 132 by the hypotube until the prongs 164 reach the next pair of grooves 162 in the guide 132, at which point the prongs 164 recoil outwardly into those grooves 162. However, the prongs 164 can have blunt or otherwise not sloped proximal surfaces such that when the hypotube 120 is pulled proximally, the prongs 164 do not disengage from the grooves 162 and therefor prevent the plow 126 from moving proximally along with the hypotube 120. This breaks the frictional engagement between the plow 126 and the hypotube 120 and allows the hypotube to move proximally relative to the plow 126. In so doing, the plow 126 prevents the clips 130 from moving proximally along the hypotube 120 as the most proximal of the clips 130 abuts the distal end of the plow 126. This breaks the frictional engagement between the clips 130 and the hypotube 120 and allows the hypotube to also move proximally relative to the clips 130. In so doing, as distal end of the hypotube 120 can slide proximally out from within the most distal clip 130, allowing that clip to resiliently return toward its natural crimped configuration and become secured onto one or more sutures 131 inserted into lumen of the hypotube 120, as shown in FIG. 17A. The number of pairs of grooves 162 in the clip guide 132 can correlate to the maximum number of clips 130 that can be loaded into the device 100. The device 100 is shown fully loaded with clips 130 in FIGS. 23C-23F, with the prongs 164 positioned in the most proximal pair of grooves 162. The plow 126 can ratchet forward along the guide 132 one clip length after each clip 130 is deployed. The vacuum tube 122, plow 126, hypotube 120, and clip guide 138 can all be fixed rotationally such that they maintain a fixed rotational alignment to one another and to the handle portion 102.

The outer tube 132 can be positioned around the vacuum tube 122 and the clip guide 138. A proximal end of the outer tube 132 can be fixed to the handle portion 102 via the adapter 136 (see FIGS. 24 and 25) such that the outer tube 132 does not rotate or translate relative to the handle portion. The outer tube 132 can comprise a lateral opening 134 that is axially aligned with the opening in the vacuum chamber 124 to allow access to the inner lumen to draw out the free end of the suture, as shown in FIG. 17B.

Figure 18F:
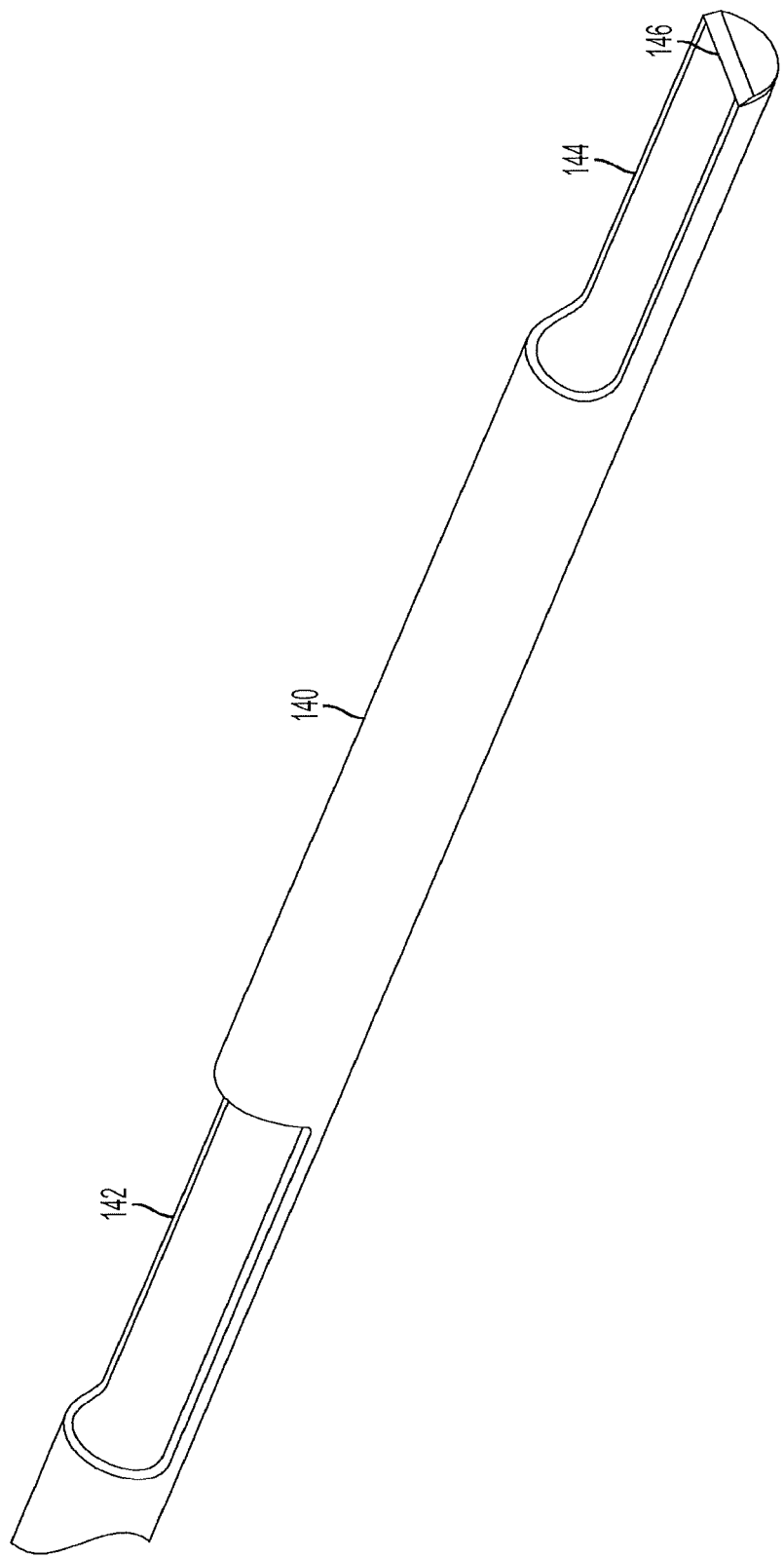

As shown in FIGS. 18E and 18F, the shaft portion 104 can also include a knife portion 140 positioned around the outer tube 132. The knife portion 140 also includes a lateral opening 142 that is axially aligned with the opening in the vacuum chamber 124 to allow access to the inner lumen to draw out the free end of the suture. The knife portion 140 can also comprise a cut-away distal end portion 144 and cutting blade 146 positioned at the distal end and oriented perpendicular to the longitudinal axis. When assembled, as shown in FIG. 17B, the blade 146 is positioned just distal to the distal end of the outer tube 132 and the distal end of the clip guide 138. The blade 146 can cover more than 50% of the cross-sectional area of the knife portion 140 such that when the knife portion 140 rotates, the blade 146 shears across the distal end of the clip guide 138 can cuts any sutures passing into the inner lumen of the hypotube 120, the distal end of which can be located just proximal to the distal end of the clip guide 138. The knife portion 140 can further comprise a slot 148 located near the proximal end of the knife portion. The slot 148 can engage with the actuation mechanism of the handle portion 102 to allow the knife portion to be rotated. The adapter 150 can couple the proximal end of the knife portion 140 to the handle portion 102 to prevent axial motion of the knife portion (as shown in FIGS. 24 and 25).

The longitudinal axis of the hypotube 120 can be offset upward from the longitudinal axis shared by the vacuum tube 122, the outer tube 132, and the knife portion 140. This allows the blade 146 to be positioned below the clips 130 and the suture when the knife portion is not actuated, and then allows the blade 146 to rotate across the axis of the suture and hypotube when the knife portion is actuated.

The suture door 152 can be mounted around the knife portion 140 in order to cover and uncover the vacuum chamber 124 and lateral openings 134 and 142. The suture door 152 can be slidable along the outer surface of the knife portion 140, either manually or via mechanical actuation, to selectively open and close the lateral access to the inner lumen of the vacuum tube 122. When the suture door 152 in the closed position (e.g., in FIG. 17A) a low pressure can be maintained in the inner lumen of the hypotube 120, allowing a suture 131 to be drawn into the distal opening of the hypotube. When the suture door 152 is moved to an open position (see FIG. 17B), the vacuum in the hypotube is reduced as air can be drawn directly through the lateral openings 142, 134, through the vacuum chamber 124 and into the vacuum tube, bypassing the narrowing lumen of the hypotube. When the suture door 152 in the open position, a suture 131 drawn through the hypotube can be manually accessed and drawn laterally out through the lateral openings 134, 142, as shown in FIG. 17B. This can allow a user to grasp the free end of the suture 131 and adjust the tension in the suture prior to deploying a clip 130 onto the suture.

Figure 19A:
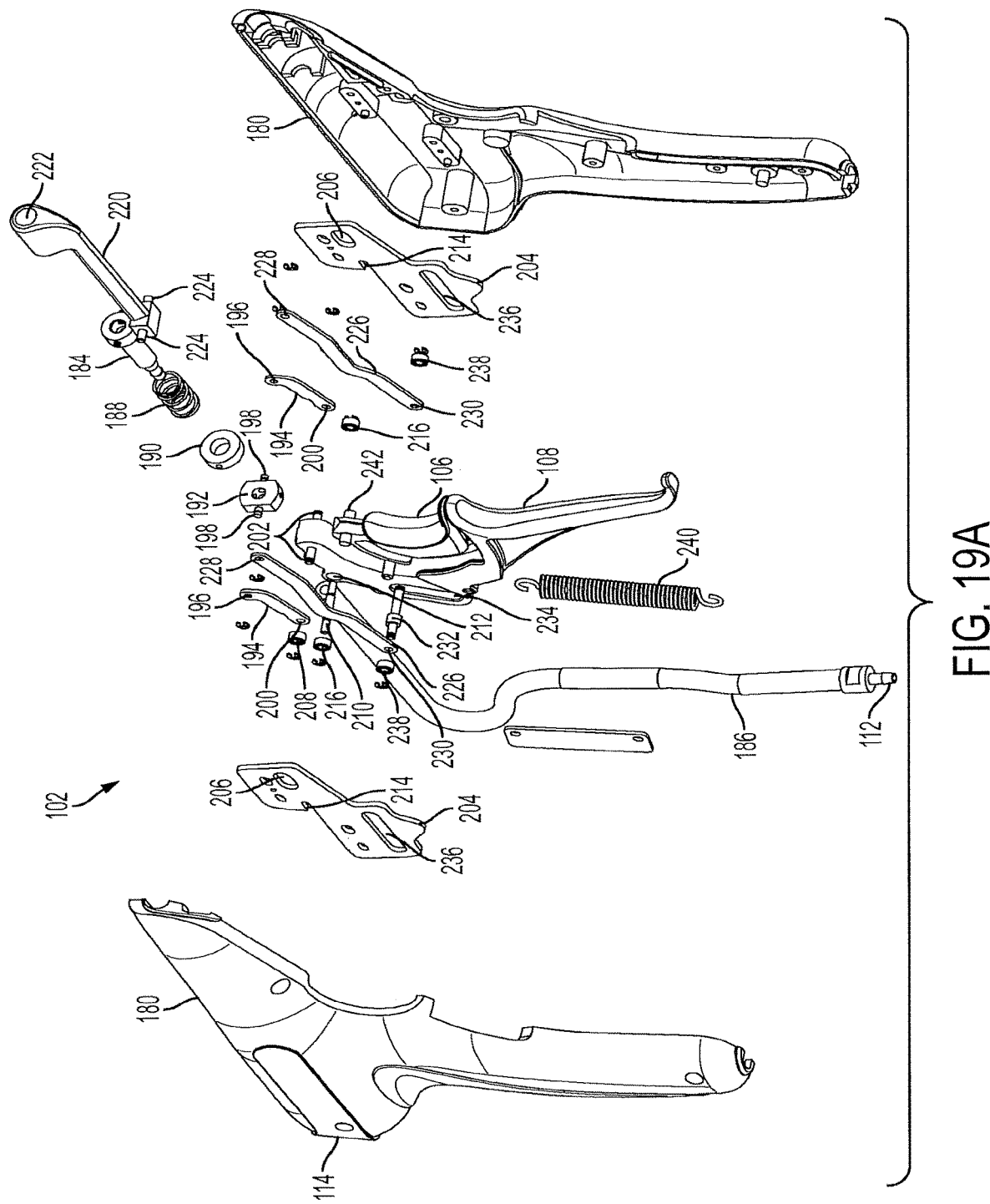
FIG. 19A is an exploded view of a handle portion of the device of FIG. 17A.
Figure 19B:
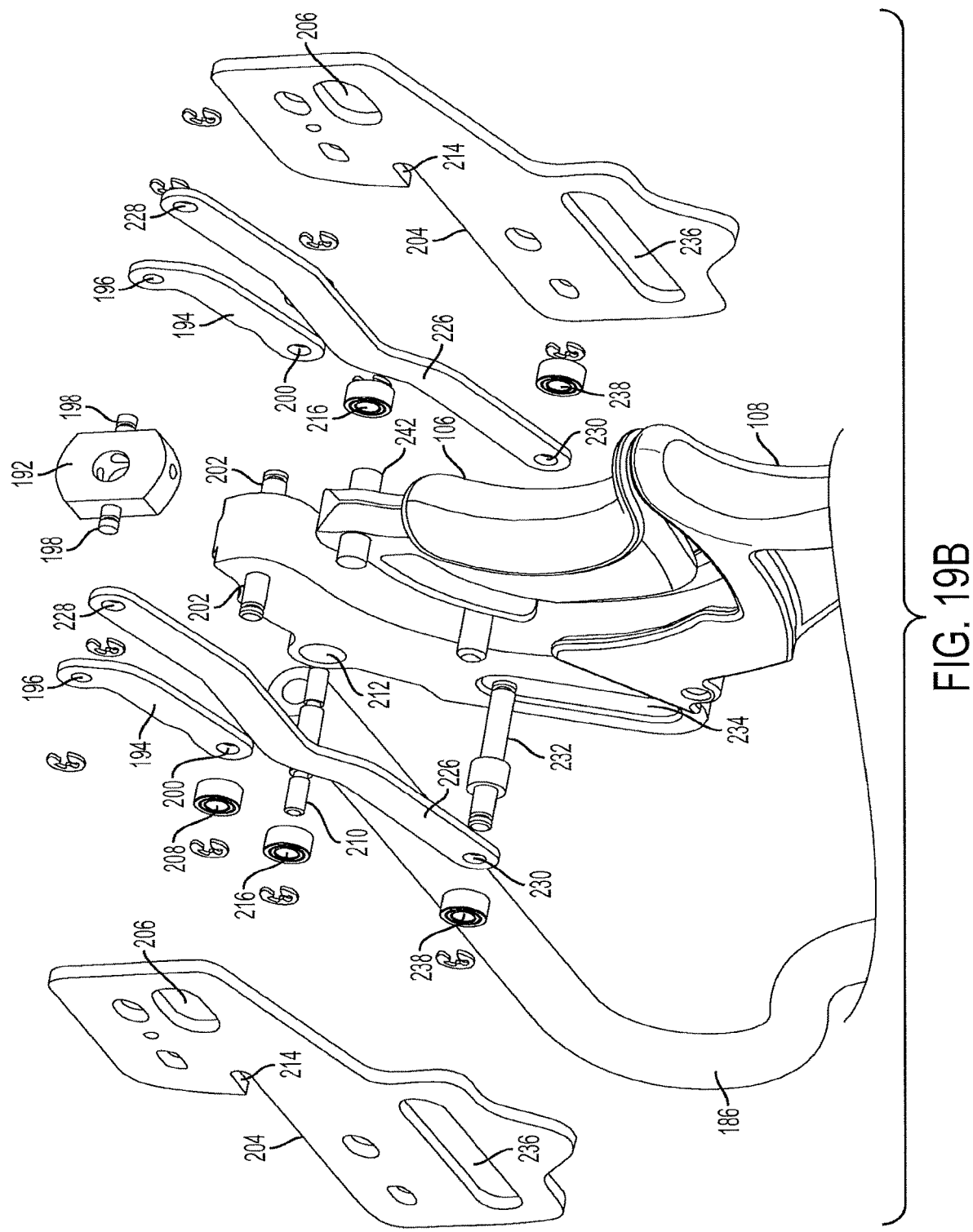
FIGS. 19B and 20 are enlarged views of portions of FIG. 19A.
Figure 20:
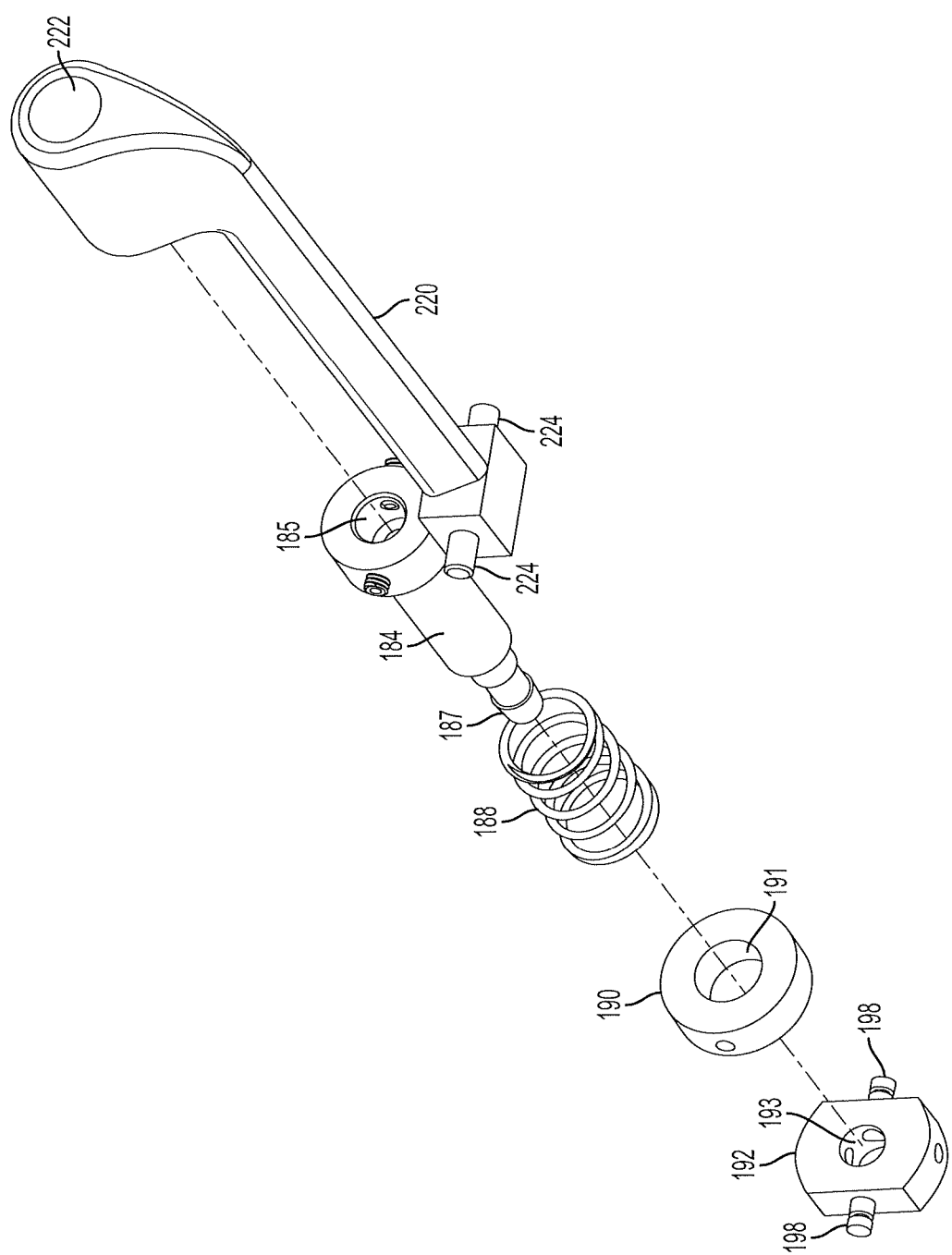
Figure 21:
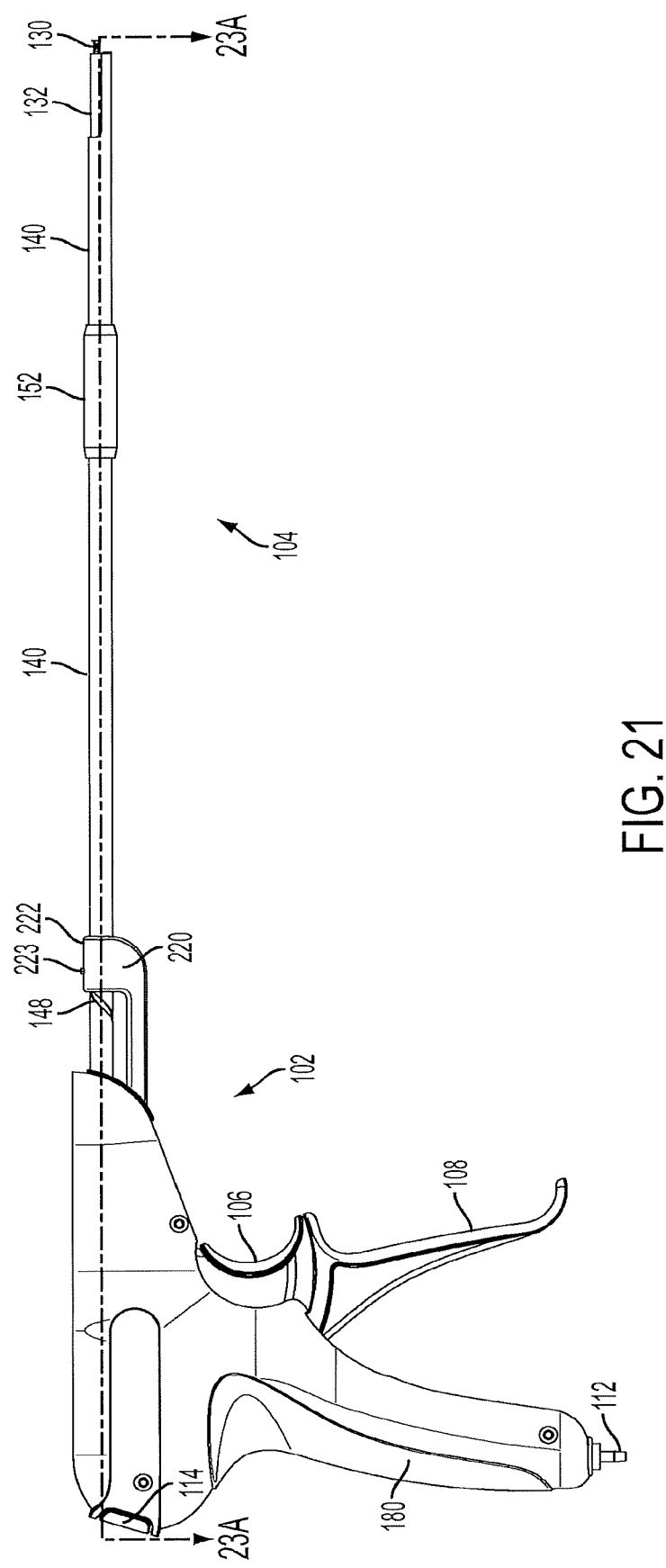
FIG. 21 is a side view of the device of FIG. 17A.
Figure 22:
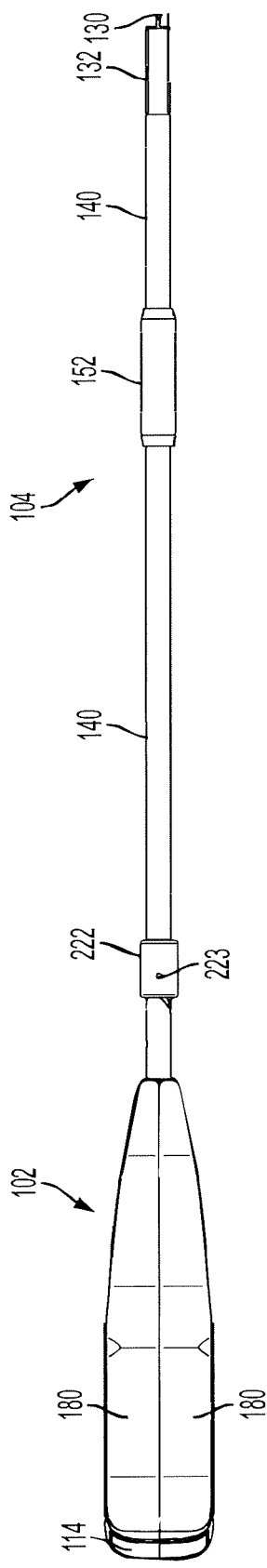
FIG. 22 is a top view of the device of FIG. 17A.
Figure 24:
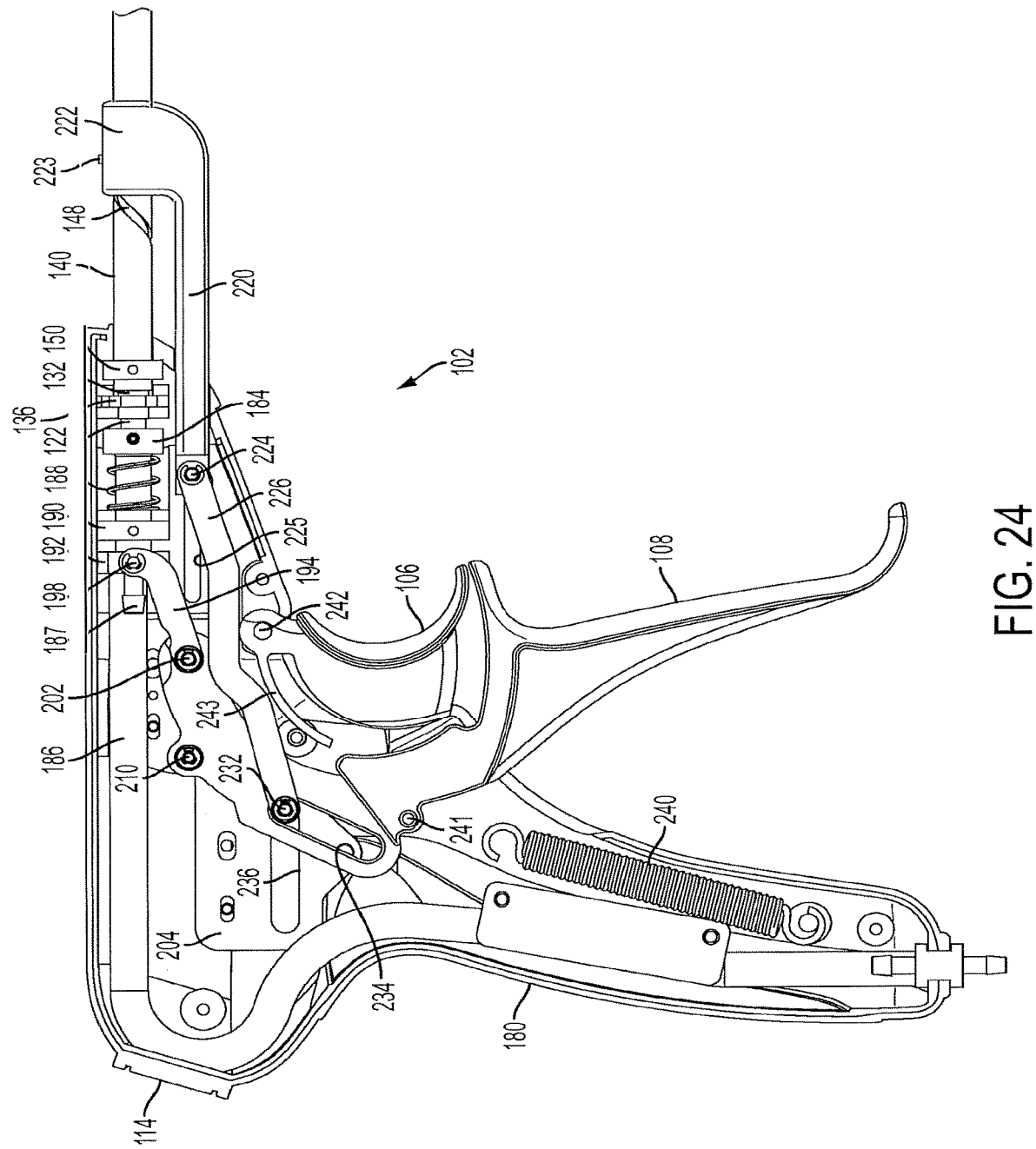
FIG. 24 is a side view of the handle portion of the device of FIG. 17A with a portion of the housing removed.
Figure 25:
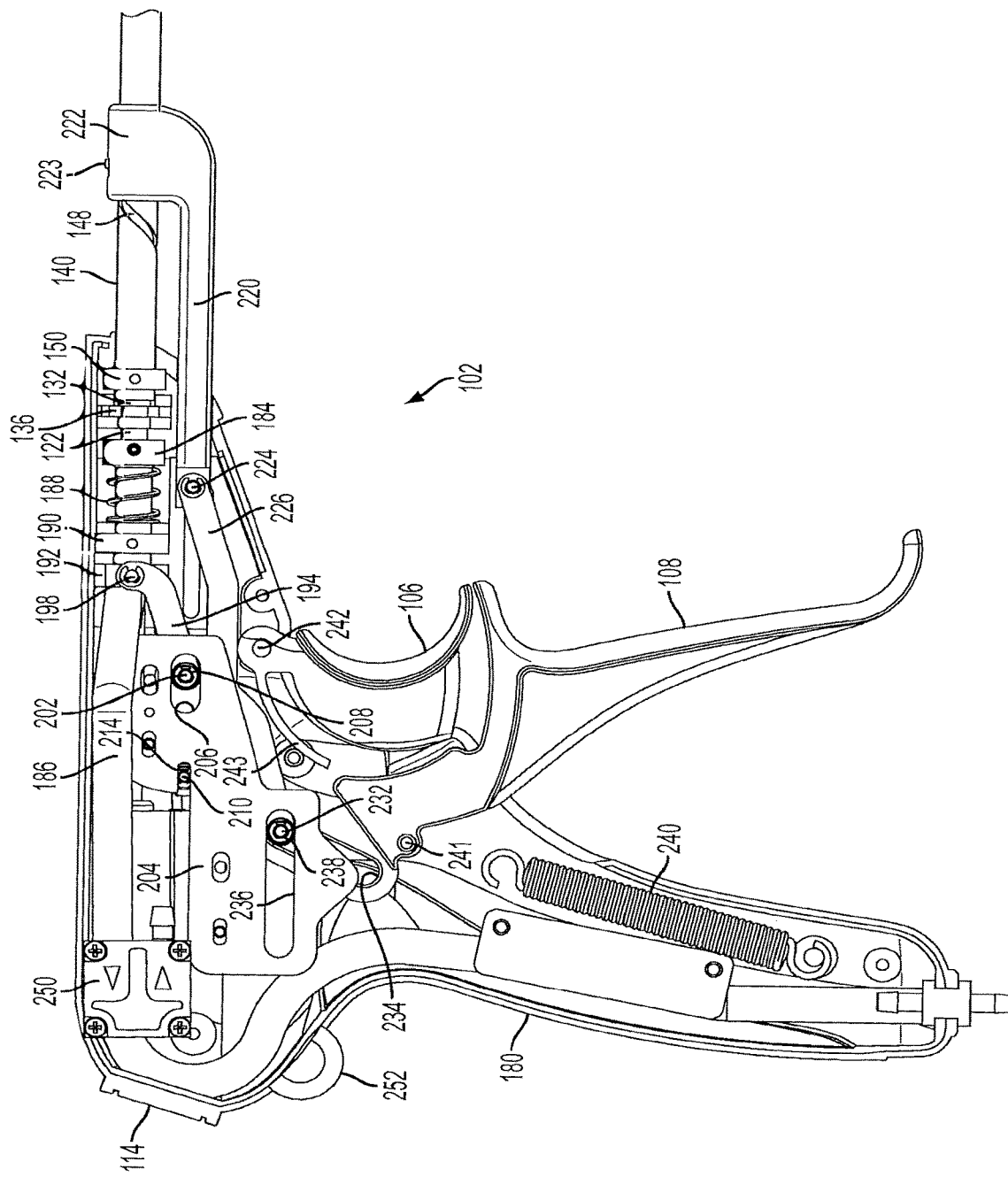
FIG. 25 is a side view of the handle portion of an alternative embodiment of the device of FIG. 17A with a portion of the housing removed.

The handle portion 102 of the device 100 is shown in FIG. 17A (perspective view), FIGS. 19A, 19B, and 20 (exploded views), FIGS. 21-22 (side and top views), FIGS. 23A-23B (cross-sectional top views), and FIGS. 24-25 (cross-sectional side views). The handle portion 102 can comprise housing portions 180 that enclose most of the actuation mechanisms, provide a hand grip, and mounting locations for some other components of the device 100.

In the illustrated embodiment, the proximal end of the vacuum tube 122 is coupled to a vacuum hose adapter 184 mounted within the housing 180. A spring 188 is positioned around the vacuum hose adapter 184 and mounted within the housing such that the vacuum hose adapter 184 and the vacuum tube 122 can be actuated axially but prevented from rotating. The vacuum hose adapter 184 is coupled to a vacuum hose 186, which can be coupled to an external vacuum source adapter 112 and/or be coupled to a vacuum source included within the housing 180. A proximal end of the spring 188 abuts a collar stop 190 mounted in fixed position within the housing. The vacuum hose adapter 184 passes through the collar stop 190 and is fixed to a pivot collar 192. The pivot collar 192 includes lateral pins 198 that pivotally engage openings 196 at one end of links 194. Openings 200 at opposite ends of links 194 pivotally engage pivot pins 202 that extend fixedly from an upper portion of the lever 108. Roller bearings 208 are rotatably attached to the ends of the pins 202 outside of the links 194. The roller bearings 208 are positioned within horizontal slots 206 of plates 204, which are mounted to the housing 180.

The lever 108 can include a lower extension that protrudes outside of the housing and provides a manual actuation location. An upper portion of the lever 108 adjacent to the pins 202 can comprise opening 212 that is mounted around an intermediate portion of an anti-rotation pin 210 via one or more roller bearings 216. The ends of the pivot pin 210 are slidably engaged in the notches 214 in the plates 104.

The lever 108 can further comprise a slot 234 to the rear of and below the opening 212. The slot 234 is mounted around a pin 232 that can slide transversely along the slot. The pin 232 is rotatably engaged with openings 230 at lower-rear end of respective links 226 on either side of the lever 108. The lateral ends of the pin 232 are slidably engaged via roller bearings 238 within horizontal slots 236 in the plates 204.

Openings 228 in upper-front ends of the links 226 are pivotally coupled to pins 224 of a knife actuator 220, as shown in FIGS. 20 and 24. The pins 224 are also slidably engaged in horizontal slots 225 (FIGS. 24, 25) in the housing 180. The knife actuator 220 comprises a forward collar 222 positioned outside of the housing 180 and mounted around the knife portion 140 of the shaft assembly. The collar 222 includes a vertical pin 223 that extends downwardly into the slot 148 in the knife portion 140.

The vacuum trigger 106 can be mounted to the housing 180, such as via pivot axis 242 and spring arm 243, such that depressing the trigger 106 mechanically and/or electrically controls the level of vacuum applied to the vacuum tube 122. The vacuum trigger 106 can be used to initially draw a suture or sutures 131 into the hypotube and optionally out through the lateral openings 134, 142 to tension the suture as desired. When the suture 131 is tensioned as desired and ready to be secured with a clip, the vacuum trigger 106 can be released and the lever 108 can be actuated.

When the lever 108 is pulled rearwardly relative to the housing 180, the lever is initially prevented from pivoting due to the anti-pivot pin 210 being constrained in the notches 214 of the plates 204. Thus, the lever 108 is initially only allowed to translate rearwardly about the length of one clip 130. During this initial rearward translation, the pins 202 slide rearwardly along substantially the entire length of the slots 206, which can be about the length of one clip 130. The pin 232 also moves partially along the horizontal slots 236 in the plates 204 but does not translate along the vertical slot 234 in the lever 108 yet. This initial horizontal translation of the lever 108 causes the links 194 to pull the vacuum hose adapter 184 rearwardly, compressing the spring 188, and causing the vacuum tube 122 and hypotube 120 to also move proximally about the length of one clip 130. The clip plow is held still due to the positive engagement of the prongs 164 in the notches 162, and the hypotube is pulled out from within the most distal clip 130, causing the clip to deploy off the hypotube and onto a suture.

Also during the initial horizontal translation of the lever 108, the links 226 move rearwardly and pull the knife trigger 220 rearwardly about the length of a clip 130. This causes the pin 223 in the collar 222 to move proximally along an axial portion 170 of the slot 148 (see FIG. 18E). As the pin 223 moves along the axial portion 170 of the slot 148, the knife portion 140 is not caused to rotate. However, subsequent proximal movement of the pin 233 along the helical portion of the slot 148 causes the knife portion 140 to rotate and cut the suture after a clip 130 is deployed.

The subsequent proximal movement of the pin 223 can be caused by further pulling of the lever 108. After the initial rearward translation, the anti-rotation pin 210 exits the notches 214 as is free to move upwardly and rearwardly. This allows the lever 108 to begin to rotate about the pins 202 while the slots 206 prevent the lever from translating any further rearwardly. As the lever pivots about the pins 202, the pin 232 continues to translate rearwardly along the slots 236 of the plates 204 and being translating along the slot 234 in the lever 108. As the pin 232 translates further rearwardly, it pulls the links 226 further rearwardly, which pulls the knife trigger 220 further rearwardly, causing the pins 224 to slide rearwardly along the slots 226 and causing the collar 222 and pin 223 to move further rearwardly, which rotates the knife portion 140, as discussed above.

After the knife portion 140 is sufficiently rotated to cut the suture 131, the lever 108 can be released. A spring 240 can be attached between the housing and the lever 108 (e.g., at the point 241) to cause the lever to rotate back to the point where the anti-rotation pin 210 reaches the plates 204, and then the spring 188 can urge the lever 108 to translate forward as the anti-rotation pin 210 re-enters the notches 214 and the actuation process reverses itself.

As the lever translates forward, the vacuum tube 122 and hypotube 120 move distally. The clip plow 126 and clips 130 also move distally the same amount, about the length of one clip 130, and the prongs 164 move up one notch in the clip guide 138 such that the next clip is ready to be deployed the next time the lever is pulled.

In some embodiments, the device 100 can comprise a clip monitoring system that tracks/determines and displays the number of clips remaining loaded in the device. The device can comprise a display, such as a rear display 114 (see FIGS. 21-22), that shows how many clips remain. In some embodiments, when the last clip has been deployed, the clip monitoring system can cause the device to become locked such that lever 108 cannot be pulled. In some embodiments, the clip monitoring system can also display a lock-out indicator on the display. The display can be mechanical or electronic, analog or digital.

In some embodiments, the device can comprise a suture tension monitoring system that includes a sensor to measure tension in the suture and a display, such as the display 114 or otherwise, that shows a tension value, such as in pounds or Newtons.

In some embodiments, the device can comprise a vacuum monitoring system that determines and displays the pressure in the inner lumens and/or the amount or status of vacuum being generated or applied from a vacuum source. In some embodiments, an indicator on a display can indicate simply whether the vacuum is being applied, while in other embodiments, a level of vacuum or pressure can be displayed.

The embodiment shown in FIG. 25 includes an internal vacuum source 250 mounted within the housing. The internal vacuum source 250 can be used in lieu of an external vacuum source or as a secondary option to an external vacuum source. In some embodiments, the internal vacuum source 250 can be coupled to the vacuum house adapter 184 that is separate from the hose 186 shown, and in other embodiments, a forked hose can be used the branches to both internal and external vacuum sources. A switch 252, shown in FIG. 25, can be used to switch between the external vacuum source and the internal vacuum source 250. The internal vacuum source 250 can be powered by a battery source housed within the handle portion 102. If the battery dies, for example, the switch 252 can be used to switch to an external vacuum source. Conversely, the user can switch from an external vacuum source to the battery powered internal vacuum source 250. The battery can also power the monitoring systems and displays discussed above.

In some embodiments, the device 100 can be disposable after being used during a surgery and/or when all the loaded clips have been deployed. In other embodiments, the device 100 can be cleaned and reloaded with clips and reused. This can include moving the clip plow 126 back a more proximal position in the clip guide 138.

FIG. 26 shows another exemplary suture clip deployment device 300. The device 300 includes a handle 302, an outer tube 304, and an inner tube 306. A suture clip 322 (which can comprise any of the clips disclosed herein or equivalents) can be loaded onto a distal end portion of the inner tube 306, which extends about one clip length past the distal end of the outer tube 304. A free end of a suture or sutures 334 can be threaded through a lumen of the inner tube 306 and out through a lateral port 307, 308 that passes through both the inner tube 306 and the outer tube 304. The lateral port can comprise a slot 307 in the sidewall of the inner tube 306 and a slot 308 in the sidewall of the outer tube 304 that are aligned prior to actuation. A user can then grasp the free end of the suture 324 projecting out from the lateral port and apply a desired tension before deploying the clip 322 onto the suture.

An actuation mechanism 320 can then be manually actuated (e.g., pulled proximally) to cause the inner tube 306 to move proximally relative to the loaded clip 322 in order to deploy the clip off the distal end of the inner tube 306 onto the suture 324. As the inner tube 306 moves proximally relative to the outer tube 304, the distal end of the outer tube 304 can abut the clip 322 and force the clip to move distally relative to the retracting inner tube 306.

Further, as the inner tube 306 moves proximally relative to the outer tube 304, the slot 308 in the outer tube move across the slot 307 in the inner tube and can thereby cut or shear off a free end of a suture 324 that extends out through the port after that clip has been deployed onto the suture. The slot 308 in the outer tube and/or the slot 307 in the inner tube can be sharpened to help cut the suture 324. In some embodiments, the distal end of the inner tube can be sharpened or include a blade to cut off the free end of the suture 324 just proximal to where the clip 322 is deployed onto the suture.

The handle 302 can have any configuration, such a gun handle configuration like the device 100. The handle 302 houses the actuator 320 and optionally a spring to urge the actuator to return to the forward position after it is pulled rearward to deploy a clip 322. The handle 302 can further include various ports and/or displays, such as for the systems described below.

In some embodiments, the device 300 can include a vacuum system for drawing a suture into the inner tube, while the device 300 does not include a vacuum system in other embodiments. In embodiment including a vacuum system, the device 300 can optionally include an internal vacuum source and/or can include a connector for coupling the device to an external vacuum source.

In some embodiments, the device 300 can include a tension monitoring system, a clip monitoring system, a vacuum monitoring system, and/or a display similar to those described with regard to the device 100.

In some embodiments, the device 300 can include a lighting system. The lighting system can comprise one or more light conductors, such as optical fibers 310, that transfer light from a light source to near the distal end of the outer tube 304. The light source can be external to the device 300 or can be included in the handle 302 as part of the device 300. As shown in FIG. 26, the fibers 310 can extend through the handle 302 and through an extension arm 311 to an adaptor 312 configured to be coupled to an external light source 314. In some embodiments, the fibers 310 can be positioned between the inner tube 306 and the outer tube 308, as shown in the cross-sectional view of FIG. 27. In other embodiments, the light fibers can be positioned between the outer tube 304 and another tube (not shown) surrounding the outer tube and the light fibers in order to isolate the light fibers from the motion between the inner and outer tubes. The distal ends of the fibers 310 can provide light near the clip deployment location within otherwise dark regions within the body to assist the user during the clip deployment process. Some embodiments of the device 100 can similarly include such a lighting system.

In some embodiments, the device 300 can include a visual monitoring system configured to capture visual information from the near the distal end of the outer tube 304 and transfer the captured visual information to a proximal visual display. For example, the device 300 can include a camera or endoscope positioned near the distal end of the outer tube 304 that is coupled via wiring to an adaptor 316 extending from the handle 302 and configured to be coupled to an external monitor that a user can view to assist in the clip deployment process. Some embodiments of the device 100 can similarly include such a visual monitoring system as well.

In view of the many possible embodiments to which the principles of the disclosure may be applied, it should be recognized that the illustrated embodiments are only preferred examples and should not be taken as limiting the scope of the disclosure. Rather, the scope of the disclosure is at least as broad as the following claims. We therefore claim all that comes within the scope of the following claims.

What is claimed is:

1. A method for deploying suture clips onto sutures, comprising;
   causing a free end of a suture to enter into a distal end portion of a main shaft of a suture clip deployment device;
   causing the main shaft to move proximally relative to a handle portion of the suture clip deployment device, a first suture clip mounted around an outer surface of the main shaft and a second suture clip mounted around the outer surface of the main shaft proximal to the first suture clip, such that the first suture clip moves off of a distal end of the main shaft and onto the suture and resiliently secures to the suture, and such that the second suture clip moves toward the distal end of the main shaft; and
   after the first suture clip is secured to the suture, causing the main shaft and the second suture clip to move distally together relative to the handle portion such that the suture clip deployment device is ready to deploy the second suture clip onto another suture by subsequent proximal motion of the main shaft relative to the handle portion.

2. The method of claim 1, wherein causing the free end of the suture to enter into the distal end portion of the main shaft comprises reducing pressure within the main shaft in order to draw the free end of the suture into the main shaft.

3. The method of claim 1, wherein inserting the free end of the suture into the distal end portion of the main shaft comprises drawing the free end of the suture out of the main shaft through a proximal opening in the main shaft proximal to the distal end portion of the main shaft.

4. The method of claim 3, further comprising applying tension to the free end of the suture projecting from the proximal opening.

5. The method of claim 1, further comprising causing a blade of the suture clip deployment device to cut off the free end of the suture after the first suture clip is secured to the suture.

6. The method of claim 5, wherein causing the blade to cut off the free end comprises causing rotational motion between the handle portion and a cutting shaft positioned adjacent the main shaft, and wherein the relative motion results in the cutting of the suture.

7. The method of claim 1, wherein causing the main shaft to move proximally relative to the first and second suture clips mounted around the outer surface of the main shaft comprises causing the main shaft to move proximally relative to a pusher, the pusher being positioned adjacent to the main shaft and proximal to the first and second suture clips, such that the pusher blocks the suture clips from moving proximally along with the main shaft.

8. The method of claim 1, wherein causing the main shaft to move proximally relative to a handle portion of the suture clip deployment device comprises actuating a clip deployment trigger at the handle portion.

9. The method of claim 1, further comprising, after causing the main shaft and the second suture clip to move distally together relative to the handle portion:
  causing a free end of a second suture to enter into the distal end portion of a main shaft; and
  causing the main shaft to move proximally relative to the handle portion and the second suture clip such that the second suture clip moves off of the distal end of the main shaft and onto the second suture and resiliently secures to the second suture.

10. The method of claim 9, wherein causing the free end of the suture to enter into the distal end portion of the main shaft comprises activating a vacuum trigger at the handle portion, which causes reduction of pressure within the main shaft and draws the free end of the suture into the main shaft, the vacuum trigger being different from the deployment trigger.

* * * * *